United States Patent [19]

Santerre et al.

[11] Patent Number: 5,798,115
[45] Date of Patent: Aug. 25, 1998

[54] BIORESPONSIVE PHARMACOLOGICALLY-ACTIVE POLYMERS AND ARTICLES MADE THEREFROM

[76] Inventors: Paul J. Santerre, 866 White Ash Drive, Whitby, Ontario, Canada, L1N 7K3; Marc W. Mittelman, 4822 Crystal Rose Dr., Mississauga, Ontario, Canada, L5V 1H2

[21] Appl. No.: 799,938

[22] Filed: Feb. 13, 1997

Related U.S. Application Data

[60] Provisional application No. 60/011,699, Feb. 15, 1996 and provisional application No. 60/014,391 Mar. 28, 1996.

[51] Int. Cl.$^6$ .................................................. A61K 31/785
[52] U.S. Cl. .................... 424/423; 424/78.08; 604/29; 606/228; 623/11
[58] Field of Search .......................... 424/78.08, 78.27, 424/423

[56] References Cited

U.S. PATENT DOCUMENTS

| | | | |
|---|---|---|---|
| 4,670,444 | 6/1987 | Grohe et al. | |
| 5,219,564 | 6/1993 | Zalipsky et al. | 424/78.08 |
| 5,405,919 | 4/1995 | Keefer et al. | 525/377 |
| 5,449,720 | 9/1995 | Russell-Jones et al. | 525/54.1 |
| 5,455,027 | 10/1995 | Zalipsky et al. | 424/78.17 |
| 5,474,765 | 12/1995 | Thorpe | 424/78.17 |

FOREIGN PATENT DOCUMENTS

| | | | |
|---|---|---|---|
| 0 710 689 A2 | 5/1996 | European Pat. Off. | C08G 73/02 |

OTHER PUBLICATIONS

Shi et al: Synthesis and Characterization of Hydrolytically Labile Poly (phosphoester-urethanes) American Chemical Society (1991) pp. 141–154, Chapter 14.

Bruin et al: "Biodegradable lysine diisocyanate-based poly (glycolide-co-ε-caprolactone)-urethane network in artificial skin".

Jansen et al: "Development of polymers with anti-infectious properties", Applied Bioactive Polymeric Materials, 1987 Polymer ... Technology, 38, pp. 97–113.

Jansen et al: "Antibiotic-containing polyurethanes for the prevention of foreign-body infections", Polymeric Materials Science & Engineering, 1988, 59, 794–797.

Golomb et al: "Prevention of bacterial coloization on polyurethane in vitro by incorporated antibacterial agent", Journal of Biomedical Materials Research, vol. 25, 937–952 (1991).

(List continued on next page.)

Primary Examiner—Peter F. Kulkosky
Attorney, Agent, or Firm—Pillsbury Madison & Sutro LLP

[57] ABSTRACT

This invention relates to pharmacologically-active polymeric compounds; to substrates, such as implantable medical devices formed thereof or coated therewith; and to methods of using said compounds or said substrates for providing pharmacological agents released in response to in vivo activation at a desired location in a mammal. The polymeric material has a backbone comprising a pharmacologically-active fragment covalently linked through at least two functional groups within the backbone, wherein the backbone comprises, preferably, polyamide, polyurethane and/or polyurea linkages with, optionally, polyester, polycarbonate, polyether and/or polyvinyl linkages. The preferred pharmacological compounds are fluoroquinolines, particularly, ciprofloxacin. The pharmacologically-active compounds provide in vivo enhanced long term anti-inflammatory, anti-bacterial, antimicrobial and/or anti-fungal activity.

15 Claims, 19 Drawing Sheets

OTHER PUBLICATIONS

Phaneuf et al: "Application of the quinolone antibiotic ciprofloxacin to Dacron utilizing textile dyeing technology", Journal of Biomedical Materials Research, vol.

Ozaki et al: "In Vivo Testing of an Infection–Resistant Vascular Graft Material", Journal of Surgical Research 55, 543–547 (1993).

Karck et al: "The Efficacy of Controlled Antibiotic Release for Prevention of Polyethyleneterephthalate–(Dacron–) Related Infection in Cardiovascular Surgery", Clinical Materials 13 (1993) 149–154.

Duran et al: "Antimicrobial coatings on medial devices", Surfaces In Biomaterials Symposium, Oct. 14–16, 1992.

Ghosh:, "Synthetic Macromolecules as Potential Chemotherapeutic Agents", Polymers News 1988, vol. 13, pp. 71–77.

Veld, et al: "In–vitro Degradation of Polyesteramides Containing Poly–ε–caprolactone Blocks", Clinical Materials 13, 1993, 143–147.

Ghosh: Studies Directed Towards Polymeric Quinolone Antibiotics –Synthesis of Potential Monomers From Nalidixic Acid, pp. 790–793.

Ghosh:, "Monomers and polymers from nalidixic acid –synthesis, characterization and hydrolysis study", Process In Biomedical Polymers, 1990, pp. 335–345.

Santerre et al, Macromolecules, 24:5497–5503 (1991); Santerre et al, Journal of Biomedical Materials Research, 28:1167–1199 (1994).

Phaneuf et al, Journal of Biomedical Materials Research, 27:233–237 (1993).

Blassberger et al, Biotechnology and Bioengineering, XX:309–315 (1978).

Labow et al, J. Biomater. Sci. Polymer, Edn. 6(2):169–179 (1994).

Poiani et al, Bioconjugate Chemistry, 5(6):621–629 (1994).

BIORESPONSIVE PHARMACOLOGICALLY-ACTIVE POLYMERS AND ARTICLES MADE THEREFROM

RELATED APPLICATIONS

This application is based on U.S. provisional applications No. 06/011,699, filed Feb. 15, 1996 and No. 06/014,391, filed Mar. 28, 1996.

FIELD OF THE INVENTION

This invention relates to pharmacologically-active polymeric compounds; to substrates, such as implantable medical devices formed thereof or coated therewith; and to methods of using said compounds or said substrates for providing pharmacological agents at a desired location in a mammal.

BACKGROUND TO THE INVENTION

Medical devices, may be classified in two major groups: 1) total implantable e.g. artificial joints, heart valves, and the like; and 2) access devices associated with an exit site, hereinafter termed "AD", which may be farther divided into a) those which exit through an orifice, e.g. urinary catheters, endotracheal tubes, and the like, and b) those which cross exit transcutaneously, e.g. venous access devices, peritoneal dialysis catheters, and the like.

Devices associated with an exit site are colonized by bacteria in a time-dependent fashion, which effectively limits their long-term use. Colonization of these devices may occur through two routes; 1. the intraluminal route, acquired by improper aseptic technique; 2. the extraluminal route, following colonization of the exit site and the subcutaneous tunnel, bacteria are transported along the sinus which forms between the catheter and the host tissue. Intraluminal contamination has been significantly reduced for most applications through improved connectors and aseptic handling techniques (1, 2). In contrast, limited progress has been achieved in protecting the exit site from bacterial colonization and subsequent infection (3).

Approximately 40% of all hospital-acquired infections are related to the urinary tract (4), and urinary tract infections (UTI) are among the most common factors leading to life-threatening Gram negative sepsis (5). Currently, the commonest route of colonization for indwelling urinary catheters is via the periurethral space. Bacteria colonizing the perineum and permimeatal region adhere to the catheter extraluminal surfaces, then ascend along the catheter in the periurethral space. Even with the use of closed sterile urinary drainage systems, the risk of urinary catheter associated UTI remains in excess of 5% per day of catheterization (6).

Infections associated with percutaneous access devices (PAD) account for the second greatest source of nosocomial bacterial infections. Among the devices in this category are peritoneal dialysis catheters, central venous catheter lines for total parenteral nutrition, and chemotherapy venous access catheters. All of these devices are employed over extended periods of time, ranging from several weeks to two or more years. Endogenous organisms (e.g., *Staphylococcus epidermidis*) are the most common bacteria recovered during episodes of peritonitis (7, 8). The addition of a prosthetic device to the host increases the risk of infection four-fold (9). In the case of peritonitis, patients may require hospital admission for treatment and in approximately 20% of the patients surgery is required to remove the dialysis catheter if the infection is resistant to antibiotic therapy or is rapidly recurrent after cessation of therapy (10).

Classically, PAD catheters are fabricated from smooth latex, silicone rubbers, or polyurethanes. These materials do not allow the skin epithelial cells to permanently adhere to them either mechanically or chemically. Following implantation of a PAD catheter, the epidermal cells begin to migrate, each seeking to surround themselves completely with other epidermal cells. Under normal wound healing circumstances, the granulation tissue, which forms near the skin surface, provides an ideal bed over which these cells can migrate. The presence of a PAD catheter across the skin at the exit site prevents contact of the epidermal cells with sister cells This results in the inward migration of the epidermal cells towards the subcutaneous tissues and the development of a wet sinus tract between the surface of the skin and the tubing. Necrotic epidermal cells and keratin line the sinus tract creating an ideal environment for microbial colonization. Organisms colonizing the exit site sinus spread along the external surface of the catheter forming an adherent biofilm (11). Dacron cuffs are usually employed to prevent dislodgement of the catheter, and act as a "biological barrier" to the ingress of bacterial cells along the exit site sinus. It is the failure of host tissue integration with the Dacron cuff prior to bacterial colonization which leads to exit site-tunnel infections. Gristina (12) has described this situation as a "race to the surface". That is, if host tissue is allowed to integrate with the implanted device before bacteria are able to adhere, infection does not usually occur. This integration process can require several weeks following device implantation.

Current treatment modalities (local and systemic) are frequently associated with a high rate of re-infection. For reasons that are poorly understood, bacteria associated with foreign bodies can be 100 times or more resistant to systemically applied antimicrobials than are their planktonic (free-floating) counterparts (13, 14).

Silver coated catheters have been used to prevent exit site infections associated with chronic venous access (15) and peritoneal dialysis (16) catheters. However, long-term studies have failed to demonstrate a significant reduction in the number or severity of exit site infections. In addition, bacterial resistance to silver can develop over time and carries with it the risk of multiple antibiotic resistance (17).

Various antibiotics have also been used to coat the surfaces of catheters through non-covalent bonding. Trooskin et al. (18, 19) describes a method by which catheter surfaces were soaked in antibiotic solutions prior to their implantation. Duran et al. (20) covalently bonded a photoactivated hydrogel onto the surface of silicone materials. The antibiotic vancomycin was then immobilized within the hydrogel matrix. In both of the above studies, most of the antibiotic was essentially released over several days rather than the requisite efficacy of several weeks. The antibiotic ciprofloxacin has been impregnated into Dacron® fibres using a textile pad/heat technique which binds the drug to the fibre by non-covalent interactions. After 24 hours of exposure to a phosphate buffer washing solution, more than 80% of the drug was released from the fibres (21). Exit site infections can only be controlled when bacterial colonization is prevented for an extended period of weeks to enable complete host tissue integration.

In addition to the traditional diffusion-controlled delivery systems described by Duran (20), there exist several more sophisticated in situ drug delivery polymers which can alter the efficacy of drugs by improving target delivery and changing controlling parameters of the delivery rate. These include polymeric liposomes (22,23), bioadhesives (24,25), bioerodible polymers (26,27), chemical and physical stimuli responsive polymers (28,29) and polymer drugs (30,31). Applications of these materials have included the delivery of antitumor drugs in cancer therapy (30), insulin for diabetics (29) and antimicrobial drugs (gentamicin) for vascular grafts (32). In studies on vascular grafts, Karch et al. (32) combined gentamicin non-covalently with a fibrin sealant, which was then coated onto Dacron surfaces. This bioerodable system takes advantage of the degradative features of the biopolymer, fibrin, to release the gentamicin. The degradation process depends on the hydrolysis of amide bonds and dissolution of the fibrin network to accelerate physical release of the diffusion drug. Following implantation in a porcine model, gentamicin release was elevated for the first few days, but decreased significantly shortly thereafter. In addition, over 50% of the specimens containing the fibrin-gentamicin matrix were found to be infected upon retrieval. To-date, polymer-based antimicrobial delivery systems have failed to demonstrate in vitro or in vivo efficacy over extended periods of time.

Many sessile and sedentary plants and animals have hard, non-desquamanating surfaces and are therefore subject to the same biofouling pressures as are engineering surfaces. The "natural" antifouling properties associated with some of these non-fouling surfaces have been the subject of several research programs sponsored by the U.S. Navy and other organizations affected by biofouling activities. Extracts from Gorgonian coral (33,34), eel grass (35), and marine sponges (36) have all been employed as so-called natural antifoulants in marine coating formulations.

Although one or more of these compounds may hold promise as antifouling agents, perhaps with applications as biomaterial additives, natural compounds suffer from three major disadvantages in this regard, viz. 1) they are often available only in limited quantities; 2) the compounds are frequently difficult to synthesize de novo, and possess multiple chiral centers; and 3) their range of application is often limited both in terms of species selectivity and environmental conditions. These same considerations should be applied to emerging antimicrobial coatings applied to biomaterial surfaces. Although the concept of a "natural products" antimicrobial may hold an aesthetic appeal, there is no evidence that these compounds are either safer or more effective than those synthesized de novo.

Short-term studies with silver-sulphadiazine- and chlorhexidine-coated polyurethane vascular-access catheters showed a reduction in the incidence of exit site infections in a rat model (37). Fewer IV injected S. epidermidis cells adhered to rifampicin-treated than to untreated Dacron vascular grafts in sheep (38). Although the results of these in vivo animal studies were promising, they were all conducted over relatively short periods of time following the introduction of the biomaterial. Biomaterial-related infections can only be controlled when bacterial colonization is prevented for an extended period of time (weeks), enabling complete host tissue integration.

The bisbiguanide, chlorhexidine has shown good efficacy against surface-associated bacteria in oral environments. Chlorhexidine has a broad spectrum of activity against Gram-positive and Gram-negative bacteria as well as a variety of fungi, including Candida spp. In addition to its bacteriostatic and bactericidal properties, chlorhexidine tends to bind very avidly to mucosal tissues, tooth surfaces, and dental implant materials (39). Chlorhexidine coatings on dental implant surfaces have demonstrated excellent short-term in vivo activity against S. mutans, Porphyromonas gingivalis, and other dental pathogens (37). In addition, local tissue integration with the implants is not adversely affected by the presence of this compound (40).

Macromolecules containing nalidixic acid and its structural analogue quinolones as pendent moieties are known (56,57).

A treatment strategy which significantly reduces the rate of urinary catheter bacterial colonization would reduce the incidence of urinary tract infections and associated sequellae. In the case of an AD, infections can only be controlled when bacterial colonization is prevented for an extended period of time (weeks), enabling complete host tissue integration as was described above.

However, there remains a serious need to prevent and control exit site bacterial infections over extended periods of time.

REFERENCE LIST

The present specification refers to the following publications, each of which is expressly incorporated herein by reference.

1. Burkart J. M. 1988. ASAIO-Trans. 34:433–436.
2. Churchill D. N., Taylor D. W., Vas S. I. & Oreopoulos D. G. 1989. Perit.Dial Int. 9:159.
3. Piraino G., Bernardini J. & Sorkin M. 1987. Am.J.Kidney Dis. 10:281–286.
4. Kunin C. M. 1987 in Detection, prevention and management of urinary tract infections. Lea & Febiger, Philadelphia, pp.245–297.
5. Waren J. W., Platt R., Thomas R. J., Rosner B. and Kass E. H. 1978. N.Engl.J.Med. 299: 570–573.
6. Khoury A. E., Lam K., Ellis B. and Costerton J. W., 1992. ASAIO J. 38:174–178.
7. S.C.H. Division 1989. Canadian Peritonitis Registry. Statistics Canada, Ottawa.
8. Williams P. S., Hendy M. S. and Ackrill P. 1987. Perit.Dial. Bull. 7:183–186.
9. Christensen G. D., Baddour L. M., Hasty D. L., Lowrance G. H. & Simpson W. A. 1989. In: Bisno A. L. & F. A. Waldvogel ed. Infections associated with indwelling medical devices.American Society for Microbiology, Washington,D.C.pp.59–70.
10. Holmes C. J. & Evans R. 1986. Perit. Dialy. Bull 6:168–177.
11. Read R. R., Eberwein P., Dasgupta M. K., Grant S. K., Lam K., Nickel J. C. & Costerton J. W., 1989. Kid. Internat. 35:614–621.
12. Gristina A., 1987, Science, 237: 1588–1597
13. Hoyle B.,D., et.al., 1990. J.Antimicrob. chemother. 26:1–5.
14. Khoury A. E., et.al.,1993. Proceedings of 18th International Congress of Chemotherapy, Stockholm.
15. Groeger J. S., et.al., 1993. Ann. Surg. 218:206–210.
16. Mittelman M. W., et.al., 1994. Ann. Conf. Peritoneal Dialysis, Orlando, Fla.
17. Silver S. et al., 1988. Ann. Rev. Microbiol. 42:717–743.
18. Trooskin S. Z., Donetz A. P., Baxter J., Harvey R. A. & Greco R. S. 1987. Nephron.46:263–267.
19. Trooskin S. Z., Donetz A. P., Harvey R. A. & Greco R. S. 1985. Surgery. 97:547–551.
20. Duran L. W., Marcy J. A. & Josephson M. W. 1992. Surfaces in Biomaterials, Minneapolis, 37–41.

21. Phanluf, M. D. 1993. J. Biomed.Mater.Res., 27, 233–237.
22. Stefely J. S., Markowitz M. A. & Regen S. L. 1988. J.Am.Chem.Soc. 110:7463.
23. Szoka F. C. & Papahadjopoulos D. 1981. In: Knight C. G., ed. Elsevier, Amsterdam, pp. 51.
24. Hui H. W. & Robinson J. R. 1985. Int.J. Engl. Ed. August: 196.
25. Longer M. A., Ch'ng H. S. & Robinson J. R. 1985. J.Pharm.Sci. 74:406.
26. Heller J. 1988. J. Controlled Release. 8:111.
27. Mathiowitz E., Ron E., Mathiowitz G. & Langer R. 1989. Polym.Prepr.30:460.
28. Hsieh D. S. & Langer R. 1983. In: Roseman T. J. & Mansdorf S. Z. ed. Marcel Dekker, New York.
29. Makino K. E., Okano Mark T. & Kim S. W. 1990. J. Controlled Release, 12:235.
30. Ouchi T., Kobayshi H. & Banda T. 1990. Brit. Polym. J. 23:221.
31. Takemoto K. & Inaki Y. 1988. Acta. Polym. 39:33.
32. Karch M., Forgione L. & Haverich A. 1993. Clin. Mat. 13:149–154.
33. Keifer, P. A., Rhinehart K. L. & Hooper, I. R. 1986. J.Org.Chem. 5:4450–4454.
34. Vrolijk, N. H., Targett N. M., Baier R. E. & Meyer A. E. 1990. Biofouling. 2:39–54
35. Harrison, P. G. & Chan A. T. 1980. Mar.Biol. 61:21–26
36. Sears M. A., Gearhart D. J. & Tittschof D. 1990. J.Chem.Ecol. 16:791–799
37. Bach A., Bohrer H., Motsch J., Martin E., Geiss H. K. & Sonntag H. G. 1994. J.Antimicrob.Chemother. 33:969–978
38. D'Addato M., Curti T., Freyrie A., Agus G. B., Bertini D. 1994. Cardiovasc.Surg. 2:254–258.
39. Sodhi R. N. S., Grad H. A. & Smith D. C. 1992. J.Dent.Res. 71:1493–1497
40. Burchard W. B., Cobb C. M., Drisko C. L. & Killoy W. J. 1991. 6:418–426.
41. Remes A. & Williams D. f. 1992. Biomater. 13:731.
42. Labow R. S., et al., 1994. J:Biomater. Sci. Polym. Edn., 6, 169–179.
43. Santerre J. P., et al., 1993. J.Biomed.Mater.Res. 27, 97–109.
44. Labow R. S., Erfle D. J., Santerre J. P. 1996. Biomaterials, 17, 2381–2388
45. Santerre J. P. et al., 1994. J.Biomed.Mater.Res., 28:1187–1199.
46. Santerre J. P., Labow R. S. 1997, J.Biomed.Mater.Res. 33, in press.
47. Wang F. G. B., Santerre J. P., Labow R. S. 1997, J.Biomed.Mater.Res. 33, in press.
48. Khoury A. E., Nicholov R., Soltes S., Bruce A. W., Reid G. & DiCosmo F. 1992. Int.Biodeterior. Biodegrad. 30:187–199.
49. Mittelman M. W., et al. 1992. Biofouling 6:39–51.
50. Mittelman M. W., Nivens D. E., Low C. & White d. c. 1990. Microb.Ecol. 19:269–278.
51. Rodriguez G. G., Phippps D., Ishiguro K. & Ridgway H. F. 1992. Appl. Environ. Microbiol. 58:1801–1808.
52. Vestal J. R. & White D. C. 1989. Bioscience. 39:535–541.
53. Olsen M. W., Nickel J. C., Khoury A. E., Morck D. W., Cleeland R. and Costerton J. W., 1989, J.Infect. Dis. 159: 1065–1072.
54. Fung H. C., Khoury A. E., Oreopoulis D., Vas S. and Mittelman M. W. 1996, Peritoneal Dial. Int. 16:380–388.
55. Fung H. C., Mittelman M. W., Thorner P. S. and Khoury A. E., 1996. Urology (submitted).
56. Ghosh M. Progress in Biomedical Polymers, ed. Gebekin C. G. and Dunn R. L., Plenum Press, New York, 1990, pp.335–345.
57. Ghosh M. Polymeric Materials, Science & Engineering (1988), 59, pp.790–793.

SUMMARY OF THE INVENTION

It is an object of the present invention to provide polymeric compounds which reduce the incidence of infection, due to the presence of access devices, particularly exit site infections in transmucosal devices and percutaneous access devices. It is a further object to provide access devices either coated with said pharmacologically-active polymeric compound or formed in whole or in part of pharmacologically-active said polymeric compound.

It is a yet further object to provide a method of reducing the incidence of infection due to the presence of access devices, particularly, of exit site infections associated with percutaneous access devices.

Accordingly, in its broadest aspect the invention provides a bioresponsive pharmacologically-active polymeric material having a backbone comprising a pharmacologically-active fragment covalently linked through at least two functional groups within said backbone. By the term "pharmacologically-active fragment" is meant a chemical radical, group, entity and the like, which provides a pharmacologically-active compound by in vivo biochemical action, such as, enzymatic and non-enzymatic hydrolysis or oxidation upon the bioresponsive polymeric material. The fragment per se within the polymeric material may not be pharmacologically-active.

Preferably, the pharmacologically-active fragment is covalently, divalently-linked within the polymeric material, and in such compounds it would not be deemed to be a pendant fragment. However, additional linkages, covalent or otherwise of the fragment either to the polymer backbone or discrete radicals, groups, entities and the like are within the scope of the present invention. Thus, the drug has at least two or more reactive groups selected from hydroxyl, amine, carboxylic acid or sulfonic acid. If it is desired to form the polymeric material as a linear polymer the pharmacologically-active compound is only divalently covalently linked.

The polymeric backbone comprises one or more polyurea, polyurethane, polysulphonamide or polyamide linkages, optionally having one or more polyvinyl, polyester, polycarbonate or polyether linkages.

The invention is of particular value to those pharmacologically active compounds which are bioresponsive as hereinabove defined to provide in vivo a pharmacological active ingredient which has at least two functional groups capable of reacting with a diisocyanate to form amide, urea and or urethane linkages, such as the fluoroquinolone family of antibiotics.

The in vivo pharmacological activity generated may be, for example, anti-inflammatory, anti-bacterial, anti-microbial, anti-fungal, but this invention is not limited to such biological activities.

The present invention is of particular use wherein the pharmacologically-active fragment is formed from the antibacterial 7-amino-1-cyclopropyl-4-oxo-1-4-dihydroquinoline and naphthyridine-3-carboxylic acids described in U.S. Pat. No. 4,670,444—which issued to Groke et al. Jun. 2, 1987. The most preferred antibacterial member of these classes of compounds is 1-cyclopropyl-6-fluoro-1,4-dihydro-4-oxo-7-piperazine-quinoline-3-carboxylic acid, having the generic name ciprofloxacin. Others of this class include ofloxacin and norfloxacin.

The polymeric material of use in the practice of the invention may be linear or comprise a series of crosslinked polymer chains. The polystyrene equivalent molecular weight of the chains may range from 2,000 to 200,000, preferably 10,000 to 100,000.

The present invention provides mammalian host-responsive, bioerodable polymers which deliver sustained effective amounts of antibiotics to target tissue over desired extended periods of time. Thus, a polymer according to the invention in the biological environment of host tissue and the like, in one aspect, is subjected to released hydrolytic enzymes and oxidative species under, and in proportion to, the host's inflammatory response. This results in release of the active ingredient via the breaking of the covalent linked bonds. Thus, the materials of the invention utilize the mammal's own wound healing repair process in being degraded thereby as hereinbefore described.

In a further aspect, the invention provides a substrate coated with or comprising in whole or in part a bioresponsive pharmacologically-active polymeric material as hereinbefore defined.

The substrate may be an access device such as a catheter, so coated or formed with the polymeric material which provides sustained delivery of the antimicrobial agent during the critical tissue integration period. The substrate may be formed of a plastics material, glass or other suitable carrier for the pharmacologically-active polymeric material. Preferably, the substrate is a silicone or polyurethane material, which, preferably, has coated on a surface thereof the pharmacologically-active polymeric material to provide a so-called antimicrobial composite material (ACM).

Examples of such substrates according to the present invention includes, cardiac assist devices; cardiac replacement devices; cardiac septal patches; vascular grafts; intra-aortic balloons; percutaneous cardiac assist devices; extracorporeal circuits; A-V fistulas; dialysis components; aphoresis components; membrane oxygenation components; cardiac bypass components; pericardial sacs; contact lenses; cochleal ear implants; artificial skin; sutures; sewing rings; cannulas; separating agent; contraceptive devices; syringes; O-rings; bladders; penile implants; drug delivery components; drainage tubes; pacemaker leads; coatings for implantable wires; coating for eye glasses; urethral catheters; peritoneal dialysis catheters; CSF shunts; orthopedic implants; venous and arterial access catheters; dental implants; blood collection bags; vascular stents; angioplasty devices; laryngeal voice box implants and wound dressings.

In addition, as foreign objects in the host tissue, these materials initiate the inflammatory response. Phagocytic white blood cells, such as neutrophils and monocyte-derived macrophages and remodeling cells such as fibroblasts have the ability to migrate towards and strongly adhere to the surface of biomedical implants (41). Once at the wound site, activated neutrophils and macrophages strongly attach to the surface of the implant in an attempt to engulf it. This response can be broadly divided into non-specific and specific protective mechanisms. One of the non-specific reactions is the synthesis and secretion of enzymes and high-energy oxygen radicals by phagocytic cells. Groups of enzymes released during these processes include esterases, proteinases, phospholipases and hydrolases.

Recent studies on the mechanism of polyurethane biodegradation by Santerre and his colleagues have identified esterase and proteinase enzymes that are released by neutrophils and monocyte-derived macrophages and which can activate the hydrolytic degradation of polyurethanes (42,43, 44). Specifically, it has been shown that the kinetic reaction of an enzyme with polymer can proceed through the cholesterol esterase's active serine site 42 and either at ester or amide type linkages, including urea and urethane sites of the polymer (45–47). Enzymatic degradation processes are limited by the polymer chain chemistry, internal material structure, and the surface area of the device (45,46). By altering these properties, the rates of biodegradation for the materials can be varied.

BRIEF DESCRIPTION OF THE DRAWINGS

In order that the invention may be better understood, preferred embodiments will now be described by way of example, only, wherein.

DETAILED DESCRIPTION OF PREFERRED EMBODIMENTS

Figure 1:
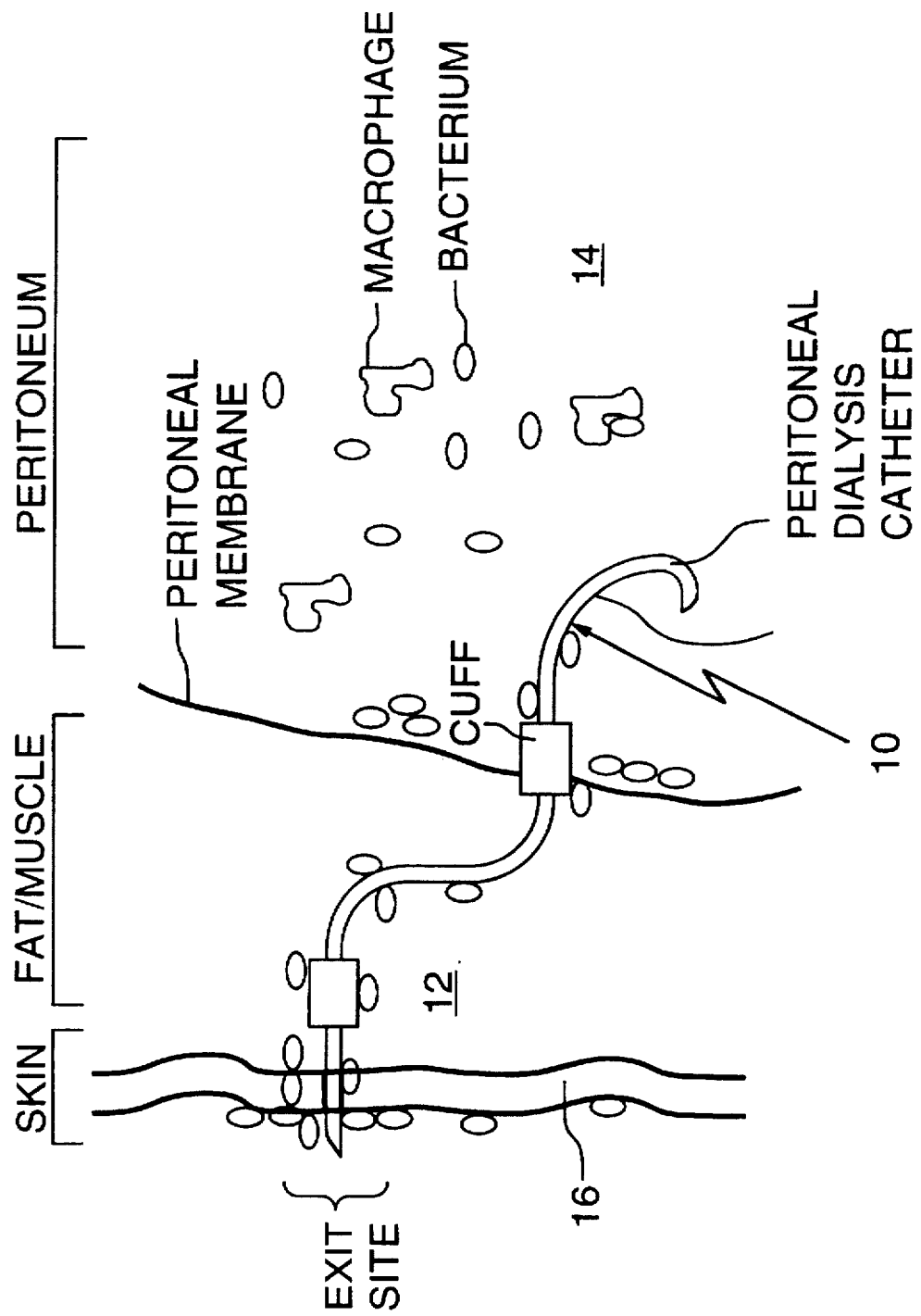
FIG. 1 shows a diagrammatic representation of a catheter according to the invention located within human tissue; 12

FIG. 1 shows generally as 10 a peritoneal dialysis catheter embedded in the fat/muscle 12 and peritoneum 14 through the skin 16. Catheter has a surface coating of a bioresponsive pharmacologically-active polymer incorporating ciprofloxacin.

Figure 2:
FIG. 2 shows a diagrammatic representation of a standard peritoneal dialysis catheter with a coating of a bioresponsive pharmacologically-active polymer according to the invention.
Figure 3:
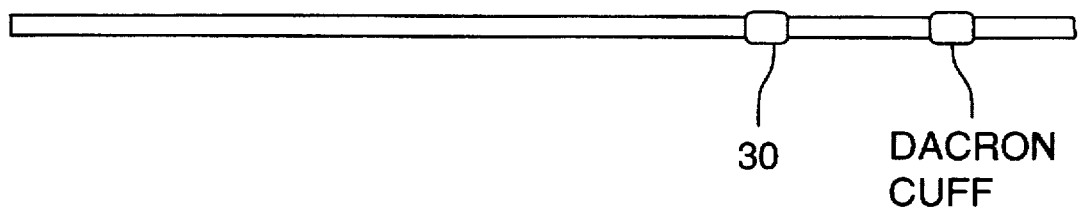
FIG. 3 shows a diagrammatic representation of a peritoneal dialysis catheter made of bioresponsive pharmacologically-active polymer.

FIGS. 2 and 3 show a standard peritoneal dialysis catheter 20 with a coating of bioresponsive pharmacologically-active polymer and a peritoneal dialysis catheter 30 made of bioresponsive pharmacologically-active polymer, respectively.

Figure 4:
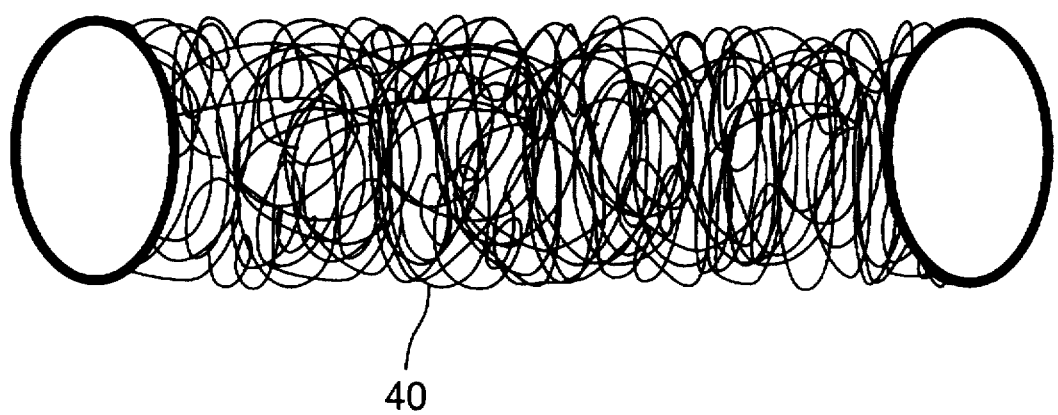
FIG. 4 shows a diagrammatic representation of a vascular graft spun on a mandrel with bioresponsive pharmacologically-active polymer.

FIG. 4 shows a vascular graft 40 spun on a mandrel with bioresponsive pharmacologically-active polymer.

Figure 5:
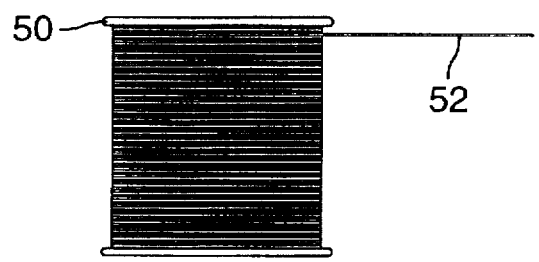
FIG. 5 shows a diagrammatic representation of a fibre according to the invention.

FIG. 5 shows a reel or bobbin 50 holding a thread, fibre or dental floss 52 formed of a bioresponsive pharmacologically-active polymer for use as an insert into body areas, which areas may be particularly susceptible to bacterial growth, such as periodontal pockets of the oral cavity; or as use as a suture.

Figure 6:
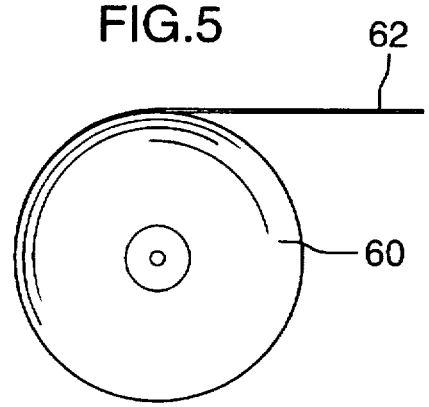
FIG. 6 shows a diagrammatic representation of a tape according to the invention.

FIG. 6 shows a reel or dispenser 60 holding a tape 62 made from a bioresponsive pharmacologically-active polymer for use as an insert into body areas which are particularly susceptible to bacterial growth, i.e. between toes, to release anti-fungal agents against athletes foot. Another example of a use for such a tape is use as a seal for screw devices, such as a dental implant, wherein bacteria often migrate into the implant along the screw hole. The tape provides both a seal between the screw and the screw hole, while simultaneously providing antimicrobial activity.

Figure 7:
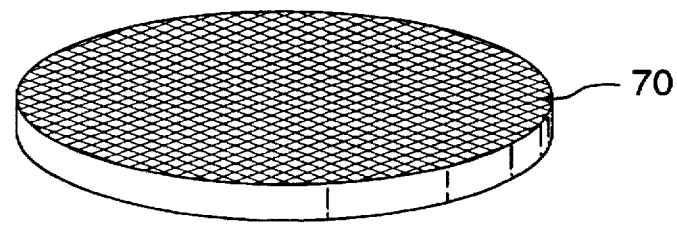
FIG. 7 shows a diagrammatic representation of a filter membrane according to the invention.

FIG. 7 shows a filter or other membrane 70 formed of a bioresponsive pharmacologically-active polymer for use in sterilizing analytical solutions or body fluids, various blood products during preparation thereof, such as intravenous fluids and the like. Another example of use of the membrane is as a wound healing patch, which requires air and fluid to pass through the membrane of the patch, but which also needs continuous treatment of antimicrobial agents to eliminate bacteria from the open wounds.

Figure 8:
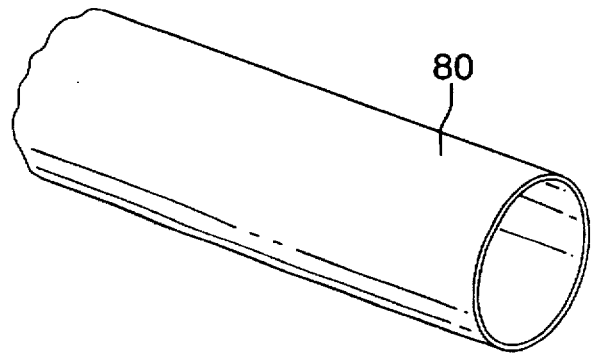
FIG. 8 shows a diagrammatic representation of a tube insert according to the invention.

FIG. 8 shows a bioresponsive pharmacologically-active polymer formed of an insert 80 into body areas, which areas are particularly susceptible to bacterial growth, i.e. ear tubes 80 used for drainage of fluids from the ear canal.

Experimental Methods

Examples of diisocyanates of use in the practice of the present invention are 1,6,diisocyanatohexane and 1,12-diisocyanatododecane, which can be reacted with the antimicrobial agent, ciprofloxacin, with or without oligomeric molecules to form polymeric materials of the invention. These pharmacological compounds have prolonged efficacious activity against access device-related bacteria. The different chain lengths of these two diisocyanates allow for varying material structure to permit tailoring of biodegradation rates. Thus, biodegradable or bioerodable polymers incorporates selected antimicrobial drugs as monomer units by reaction with the diisocyanates. The molecular chains and material morphology are such that when the inflammatory response in the tissue of the mammal is turned on, subsequently, by upregulation of the inflammatory response as a result of device implantation or other inducers of inflammation (e.g., bacterial or fungal infection), the polymeric material is biologically and specifically enzymatically, degraded to release the antimicrobial drug from the polymer chain. Release of antimicrobials proceed at effective rates until the levels of released hydrolytic enzymes are significantly lowered as a result of the diminished host response associated with tissue healing. Diagrammatic rendering of the synthesis and execution of the bioresponsive pharmacologically-active polymers, may be represented, thus:

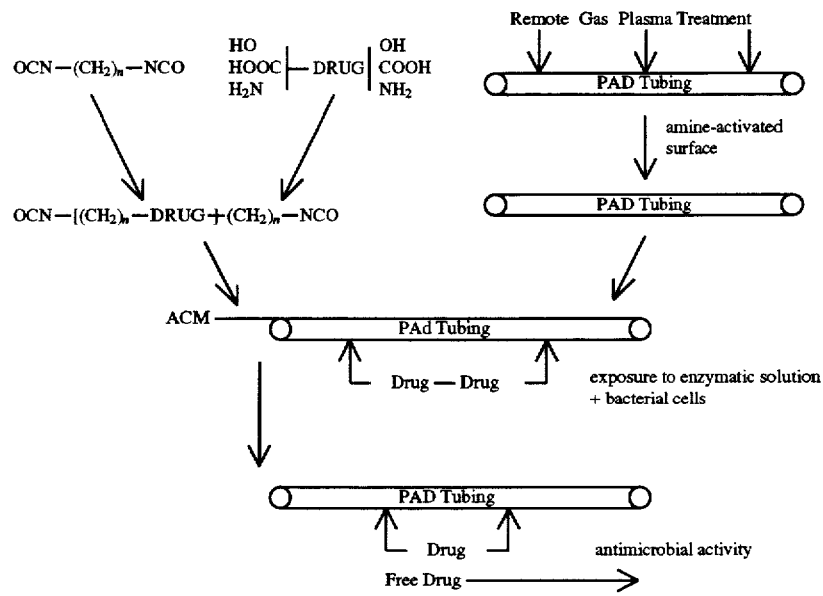

The antimicrobial polymers are synthesized in, for example, either pre-dried toluene, tetrahydrofuran, dimethylsulfoxide or other such solvents, depending on which is most appropriate based on yield and the desired polymer molecular weight. A typical bioresponsive pharmacologically-active polymer made from 1.6 diisocyanatohexane and ciprofloxacin is shown, thus:

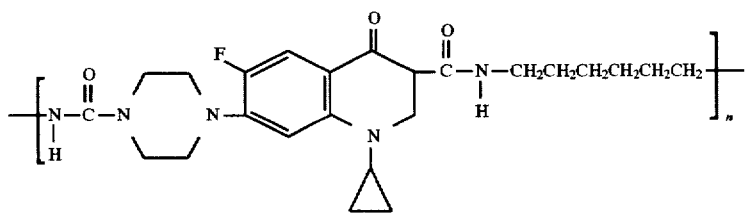

The stoichiometry of the polymer components is varied depending on the desired structure, drug activity and the method of application onto AD tube surfaces. If the antimicrobial polymer is applied to polyurethane surfaces as a coating or by solvent bonding, then the stoichiometry is such as to favor terminal antimicrobial drug monomers i.e. no free diisocyanate. Quenching of remaining free diisocyanates can be carried out with traces of methanol.

If the AD tube material (polyurethane or silicone) requires pre-activation with carboxylic acid, amine or hydroxyl groups using gas plasma or other known surface activation methods, to ensure a strong bond of the antimicrobial polymer to the tubing, then the stoichiometry is such as to favor end group diisocyanates. This diisocyanate prepolymer solution is then able to form covalent bonds with the surface-activated tubing material by reaction of free diisocyanates with active carboxylic acid, amine or hydroxyl groups.

If the polyurethane, preferably, a commercial product, used to manufacture the AD surfaces is soluble in solvents that are compatible with the antimicrobial polymers, then coatings of various thickness can be applied directly to the surface of the polyurethane via solvent casting/bonding processes.

Textured or foamed surfaces may be prepared by casting a solution of the antimicrobial polymer, containing either polyvinylpyrrolidone (PVP), polyethylene glycol (PEG), or other foaming agents, on the tubing material. The PVP or PEG is then leached out by water extraction and washing. The foam surfaces allow for the assessment of the effect of changing sample processing and sample morphology on the release of antimicrobial drugs.

Physicochemical Characterization of the Polymers.

Molecular weight analysis of the antimicrobial polymers prior to surface-bonding is carried out using gel permeation chromatography. Differential scanning calorimetry and dynamic mechanical analysis of the polymers may be performed. These latter techniques provide information on the physical properties of the polymer crystalline structure. Fourier transform infra-red (FTIR) spectroscopy of the polymers may be carried out to provide structural information on the bioresponsive pharmacologically-active polymers. Scanning electron microscopy of prepared bioresponsive pharmacologically-active polymers may be carried out in order to define surface topography of the prepared materials. Tensile strength testing of the bioresponsive pharmacologically-active polymers tubes may be evaluated using standard ASTM methods. This ensures that the mechanical properties of the original tubes remain similar to the original, unmodified tubing.

Chemical Surface Characterization.

In order to estimate the type and degree of modification at all stages in the reaction protocols and preparation of the bioresponsive pharmaceutically-active polymers, it is necessary to characterize the surface using modem surface analytical methods, such as by X-ray photoelectron spectroscopy (XPS) and secondary ion mass spectrometry (SIMS). XPS gives detailed information on the type and amount of chemical species present, while static SIMS provides detailed mass information and can usually distinguish between related species from differences in the fragmentation pattern. Further information on the degree of surface modification can be obtained by the use of angle-resolved XPS, which allows the depth of modification to be probed in a non-destructive manner.

In vitro evaluation of antimicrobial release and biodegradation kinetics.

These studies may be performed in order to assess the rates of degradation for the different antimicrobial polymer formulations. In these studies the polymers are incubated with enzyme and solutions are recovered for separation of degradation products (47). Hydrolytic enzymes related to monocyte macrophages, specifically cholesterol esterase, and neutrophils (elastase), within a pH7 phosphate buffered saline solution may be used for in vitro tests over a 3-week time frame. Both cell types are representative of the chronic and acute inflammatory response to tissue damage. Degradation products may be characterized using High Performance Liquid Chromatography (HPLC), combined with mass spectroscopy.

The degradation of bioresponsive pharmacologically-active polymer surfaces may be evaluated with the above enzymes in suspensions of urine, cryoprecipitate and complement inactivated serum for varying periods of time under static and dynamic flow conditions. Time-course fluorometric and/or BPLC measurements are made of antibiotic and other polymer degradation products in the bulk-phase solutions (48). These experiments simulate conditions of the in situ PAD environment over a period of 3–6 weeks.

Colonization Efficiency.

In vitro evaluations of the bioresponsive pharmacologically-active polymers and bioresponsive pharmacologically-active polymer formulations described hereinabove, along with native polyurethane and silicone substrata are challenged with clinically relevant bacterial strains, e.g. *Staphylococcus epidermidis*, *Pseudomonas aeruginosa*, and *Escherichia coli*. Surfaces are colonized in laminar-flow adhesion cells (49) in various suspensions, including urine and complement-inactivated serum and challenged for varying periods of time in the presence and absence of the enzymes described above. Both dynamic and static flow conditions are used in the challenge assays. Colonization is followed on a real-time basis via an image analysis system interfaced with a light microscope. Immediately following their removal from the flow system, the test materials are subjected to a gentle rinsing procedure to remove non-adherent and loosely adherent organisms. Bacteria are extracted from the bioresponsive pharmacologically-active polymers surfaces via a sonication procedure in ice-cold phosphate-buffered saline (50).

Bacteria are enumerated via standard plate counts as well as by a direct count procedure (51). Cells are incubated for 1 h. at 37° C. in a solution of 5-cyano-2,3-ditolyl tetrazolium chloride (CTC). Respiring bacteria reduce the CTC to a fluorescent formazan salt which can be visualized under epifluorescent microscopy. The suspension is then counterstained in a solution of 4',6-diamidino-2-phenylindole (DAPI), which stains both viable and non-viable bacteria and is visualized via epifluorescence microscopy. This technique is well-suited to detecting viable and viable/non-culturable bacteria in the presence of antimicrobial agents.

Effects on Bacterial Metabolic Activity.

The effects of the bioresponsive pharmacologically-active polymer antibiotics on biofilm metabolic activity are determined under conditions designed to simulate those of the in situ environment. This study determines whether cells which colonize the bioresponsive pharmacologically-active polymers are active and, therefore, potentially capable of acting as a nidus of infection. The laminar-flow adhesion cells described above are used to colonize clinically relevant bacteria described above on the bioresponsive pharmacologically-active polymers. Following an initial growth-curve study to determine dilution rates, cells are maintained in continuous culture and dosed continuously during an initial colonization phase of ca. 12 h. Bacteria are pulse-labelled under the in situ flow regime using an appropriate $^{14}C$ radiolabeled substrate e.g. glucose. Uptake experiments are conducted on biofilms developed at 12 h. intervals up to 48 h. following the initial colonization period. Label is then recirculated over the intact biofilms for 60 min. The substrata is immediately removed for extraction and activity measurements are carried out as described below. Experiments are performed in the presence and absence of the enzymes described above. Bulk-phase bacteria are also removed at 12 h. intervals following the initial colonization period and subjected to a pulse-labeling procedure as well as quantitative assays described below.

Immediately following the pulse-labeling procedure, suspensions are placed in a lipid-extraction solution, fractionated, and the lipid portion analyzed for DPM via liquid scintillation counting. The uptake in terms of carbon assimilation per cell per h. is determined for cells colonizing the bioresponsive pharmacologically-active polymers. Biofilm and bulk-phase bacteria are counted using viable-count and direct-count epifluorescent assays.

Analysis of cell membrane lipids is performed on biofilm extracts and bulk-phase suspensions. Phospholipid fatty acid analysis is conducted to determined differences in membrane lipid biomarkers (52), e.g., the ratio of saturated:monounsaturated fatty acids provides an indication of membrane "fluidity" and may be important in antimicrobial diffusion through cell membranes.

SEM Analysis.

Following colonization experiments, bioresponsive pharmacologically-active polymer materials are fixed in 2.5% glutaraldehyde, washed in PBS, dehydrated in an ethanol series, air-dried, and gold sputter-coated. The prepared specimens are then examined directly under the SEM. Both colonized and uncolonized specimens are examined and photographs taken of representative areas.

In-vitro Toxicology Studies.

Preliminary, tiered, toxicological analyses are conducted on the degraded polymer products, i.e. either oligomeric products, diamine or drugs. The cellular response of human fibroblasts and epithelial cells cultured in the presence of the polymers and potential degradation products are assessed by measuring doubling times and determining total cell count and cell death with routine dye exclusion methods. Cells are inoculated onto test substrate surfaces or into altered media (no substrate) containing degradation products and compared to empty (control) culture wells with standard media. Furthermore, the presence of degradation products in the cells are assessed by scintillation counting of the cell lysate.

In-vivo Animal Studies.

Two types of in vivo studies are performed on substrates, devices or articles according to the invention formed in whole or in part of antimicrobial composite material or polymer (ACM) according to the invention as follows.

1. Antimicrobial efficacy challenge. This study involves perimeatal inoculation of catheterized rabbits. The in vivo efficacy studies of the ACM in preventing UTI are evaluated in a previously described rabbit UTI model (53,54). New Zealand male rabbits (3.5–4 kg) are used. Initial sedation is achieved by an intramuscular injection (0.7 ml/kg) of a ketamine/xylazine mixture (29.2 mg/ml ketamine, 8.3 mg/mil xylazine). Halothane inhalation general anesthesia is then administered. A saline drip is established via cut-down to the external jugular vein. Animals are infused with 60 ml/h, in order to establish an adequate urine flow. The penis and periurethral area are cleaned with Povidone iodine solution prior to catheter insertion. The external genitalia are exposed by separating the legs and then painted with a Povidone-iodine solution. Identical 10 F silastic catheters, with and without antimicrobial polymer coatings, are used in all animals. A water soluble lubricant is used to facilitate catheter insertion and minimize trauma to the urethra. A lactose negative, streptomycin resistant E. coli isolate is used in the inoculated groups. This isolate has previously been shown to induce cystitis in a similar rabbit model. Following catheterization and connection of urine collection bags, the animals are inoculated with 100 µL of the washed bacterial suspension. A 0.5 mL syringe is used to drip the inoculum at the interface between the catheter and the urethral meatus. The inoculations are repeated on days two and three at approximately the same time each morning. No inocula are given on days 4–7. Animals are housed in a barrier isolation room within Plexiglas restraint cages and fed and watered ad libitum over the seven-day experimental period. The animals are euthanized with a Euthanol bolus at the first appearance of the E. coli, or at the end of the seven-day study period. Endpoints for the ACM treatments are time to establishment of E.coli in the urine, bacterial bioburden, and tissue inflammation score.

2. Biocompatibility assays. Two types of biocompatibility assays are performed. The first utilizes the same rabbit model described above, without a bacterial challenge. In this model, any inflammatory changes occurring in the urethra are evaluated. Histological changes in the urethra are evaluated using a previously established inflammatory index (58) as described below. The second bicompatability assay involves a longer-term implantation of antimicrobial polymer coated onto tubing and control surfaces (i.e. uncoated tubing) in the paraspinal region of pigs. Male Yorkshire-Landrace pigs (18–20 kg) are used in the studies (55). All animals receive a mixture of Ketamine, atropine, and acepromazine prior to anaesthesia with nitrous oxide/Halothane. The animals are intubated and allowed to breathe spontaneously. Transverse incisions are made along the paraspinal region. Small tunnels are made to create a space for antimicrobial polymer coated onto tubing and control surface placement into the subcutaneous tissue or the paraspinal muscle with minimal disruption of the tissue immediately surrounding the material. Incisions are closed with resorbable polyglycolic acid sutures. Six control and six antimicrobial polymer coated tubes are implanted along each side of the paraspinal region. The catheters are retrieved every two weeks over a 6 week period. A small cross-section of the material and surrounding tissue is submitted for histological analysis. Specimens are fixed in buffered formalin and stored at 4° C. Specimens for histological examination are paraffin-embedded and thin-sectioned prior to hematoxylin-phloxine-safranin (HPS) staining. The stained thin sections are evaluated in a blinded fashion. Inflammatory zone size, giant cell and PMN infiltration, and lymphocyte numbers are used as histological inflammation endpoints as previously described (55). The tissue inflammation score for the antimicrobial polymer coated onto tubing and control surfaces are compared using a non-paired Students-t test.

EXAMPLES

The following examples illustrate the preparation of bioresponsive pharmacologically-active polymers according to the invention.

Example 1

This is an example (S1) of a bioresponse-pharmacologically active copolymer (BR-PAC) synthesized with hexamethylene diisocyanate (HDI) (0.4 grams), ciprofloxacin HCl (0.4 grams) and Jeffamine-900® polyether terminated with amines, (1.08 grams). The BR-PAC was made using a 2:1:1 stoichiometric combination of the above respective compounds, combined with dibutyltin dilaurate catalyst (6 mg). Synthesis was carried out by dissolving ciprofloxacin HCl in dimethylsulfoxide solvent and heating to 70° C. Subsequently, the ciprofloxacin was reacted with HDI for two hours at 70° C., Jeffamine-900 polyether diamine was added and the material reacted overnight, under nitrogen in a tin foil-covered reactor to reduce the degradation of the pharmacological by light. As the polymerization proceeded the polymer precipitated out. At the end of the reaction the precipitated polymer was filtered, washed with distilled water and dried at 50° C. in a vacuum oven. The final polymer was dark yellow, hard and brittle. It had a polystyrene equivalent molecular weight of $2.3 \times 10^4$.

Example 2

This example (S2) is similar to S1 with the exception of the order in which reactants were combined during the reaction.

Ciprofloxacin HCl was dissolved as was described in Example 1 and added to a reaction mixture of HDI and Jeffamine-900polyether diamine which had been reacted at 45° C. for 2 hours. The resultant mixture was reacted for two hours at 60° C. and then cooled. While the reaction solution was maintained at 60° C., no precipitation of polymer was observed. Upon cooling below 60° C., the polymer precipitated out of solution. In Example S1 it was hypothesized that the initial product of the reaction between HDI and ciprofloxacin HCl precipitated out of solution as the reaction proceeded because formation of extended HDI/ciprofloxacin sequences became insoluble. The synthesis of S2 shows the effect of using a more soluble diisocyanate, i.e. the product of HDI and Jeffamine-900 polyether diamine, 2:1 molar ratio, respectively to react with ciprofloxacin HCl. This has the effect of reducing the size of the HCl-ciprofloxacin segments in the polymer to increase the overall solubility of the polymer. The final polymer was light yellow, hard and brittle. The polystyrene equivalent molecular weight was $1.5 \times 10^4$.

Example 3

This example (S3) is similar to S2 with the exception that the polymerization was carried out overnight in order to assess if precipitation occurred when the reaction was carried out for an extended period of time, i.e. over 13 hours. The polymer resembled the materials generated in Example S2 and precipitated out only upon cooling from 60° C. Preliminary antimicrobial MIC testing with this material showed that it was able to effectively kill *P. aeruginosa* bacteria using the methods described below in Example 7.

Example 4

This example (S4) is similar to S1 with the exception that the addition of Jeffamine-900 polyether diamine occurred immediately following the mixing of HDI and ciprofloxacin HCl. Rather than the HDI and ciprofloxacin HCl reacting for 2 hours at 70° C., these materials were allowed to react only for five minutes and then Jeffamine-900polyether diamine was added. As in Example 3, this effectively reduces the size of the HDI/ciprofloxacin component in the final polymer because there is less time for these two reagents to react prior to having the Jeffamine-900 polyether diamine molecules competing with ciprofloxacin for reaction with the isocyanate sites in HDI. Following the addition of Jeffamine-900 polyether diamine the reaction proceeded for 22 hours at 65° C. The polymer did not precipitate until it was cooled, indicating that the size of the HDI/ciprofloxacin component was controlled, as for polymer S3 in Example 3.

Example 5

This example (S5) demonstrates that the BR-PAC can be synthesized with diisocyanates differing from those used in examples S1–S4. Dodecyl-diisocyanate (DDI) was used (0.61 g) to react with Ciprofloxacin HCl (0.4 grams) and Jeffamine-900 polyether diamine (1.08 grams). The BR-PAC was made using a 2:1:1 stoichiometric combination of the above respective compounds, combined with dibutyltin dilaurate catalyst (6 mg). The material synthesis was carried out by first dissolving ciprofloxacin HCl in dimethylsulfoxide solvent and heating to 70° C. Subsequently, ciprofloxacin was reacted with HDI for a few minutes and Jeffamine-900 polyether diamine was immediately added. The resultant material was left to react overnight at 60° C. Complete reaction was carried out in a tin foil-covered reactor in order to reduce the degradation of the drug by light. During the overnight reaction period, this polymer had precipitated out of the reaction solution at 60° C. Synthesized materials were then washed with distilled water and dried at 50° C. in a vacuum oven. The final polymer was yellow and more elastomeric than BR-PAC synthesized with HDI (Examples 1–4). The polymer was easily precipitated out of water and thus produced higher yields of product. These two observations reflect the greater chain length of the diisocyanate and its ability to significantly influence both water solubility and mechanical properties.

Figure 9:
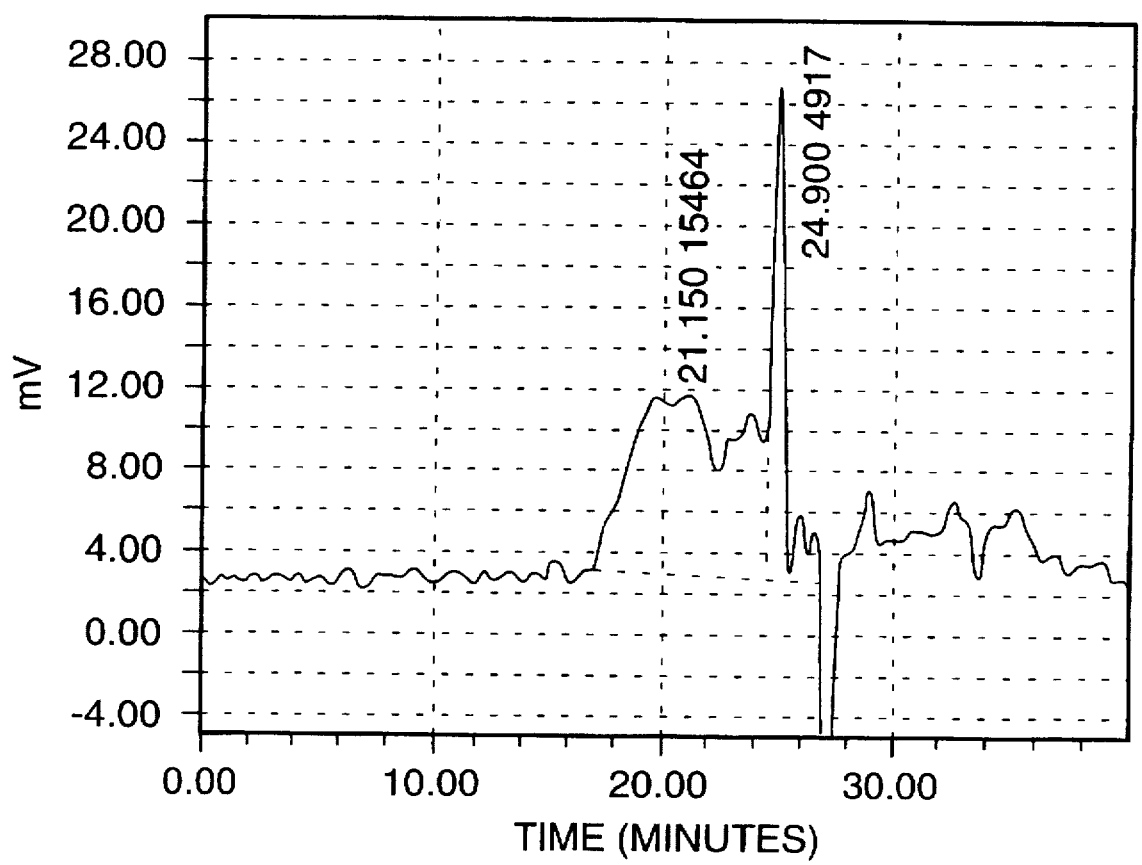
FIGS. 9–17, and 19–24 show gel permeation chromatograms (GPC), high performance liquid chromatograms (HPLC), or Uw spectral charts.

The average molecular weight values of S5 are given in the gel permeation chromatogram shown in FIG. 9. The number average molecular weight is approximately $1.3 \times 10^4$ and the weight average molecular weight is approximately $1.8 \times 10^4$. The chromatogram also shows that the polymer has a bimodal peak.

Example 6

This example (S6) is similar to S5, but used a 10-fold increase in catalyst concentration (60 mg). Changing the catalyst concentration did not influence the appearance of the polymer synthesized in Example S5. Following the addition of Jeffamine-900 polyether diamine, the mixture was reacted for 26 hours. The polymer remained in solution for 1.5 hours prior to precipitation at 60° C. The final polymer was yellow and elastomeric in nature.

Example 6A

This example (S12) demonstrates that the BR-PAC can be synthesized with different oligomeric components incorporating hydrolysable linkages and differing from those used in examples S1–S4. Dodecyl-diisocyanate (DDI) was used (0.57 g) to react with ciprofloxacin HCl (0.4 grams) and polycaprolactone diol (PCL) of molecular weight 2000 (2.06 grams). The latter molecule is an oligomeric polyester compound with terminal hydroxyl groups. The BR-PAC was made using a 2:1:1 stoichiometric combination of the above respective compounds, combined with 6 mg of the catalyst (dibutyltin dilaurate). The material synthesis was carried out by first forming a prepolymer by reaction of PCL of molecular weight 2000 with DDI and tin catalyst, at 65° C. for 3 hours in DMSO. Subsequently the ciprofloxacin HCl was dissolved in dimethylsulfoxide solvent, heating to 70° C. and then adding triethylamine as acid scavenger. The ciprofloxacin solution was reacted with the prepolymer for 40 hours at 65° C. The complete reaction was carried out in a tin foiled covered reactor in order to reduce the degradation of the drug in the presence of light. This polymer remained in solution until the reaction vessel was cooled to room temperature. The synthesized materials were then washed with distilled water and dried at 50° C. in a vacuum oven. The final polymer was yellow and elastomeric in nature. The polymer was easily precipitated in water, and yields greater than 70% were obtained. The weight average polystyrene equivalent molecular weight was $2.4 \times 10^4$.

Figure 10:
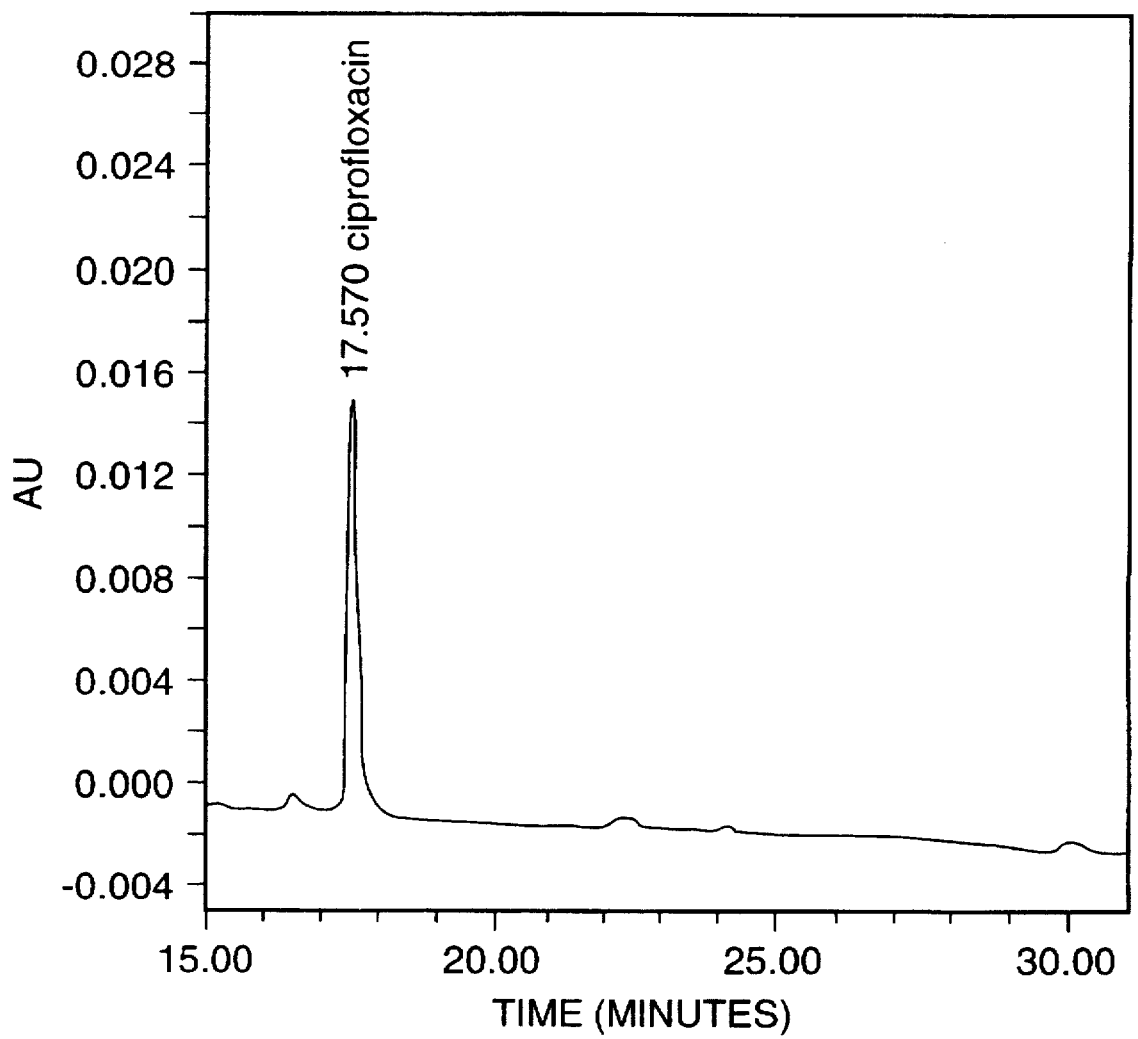
Figure 11:
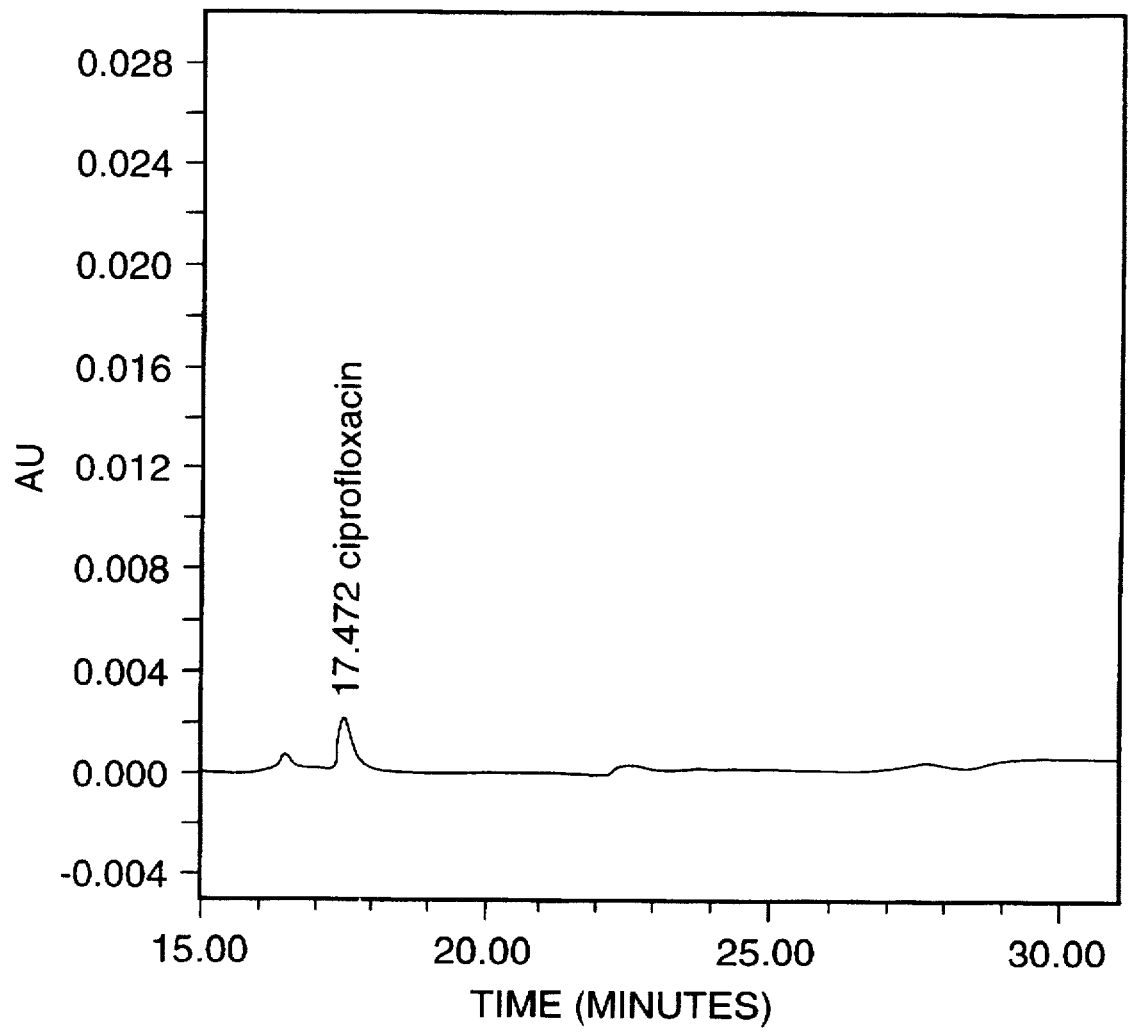
Figure 12:
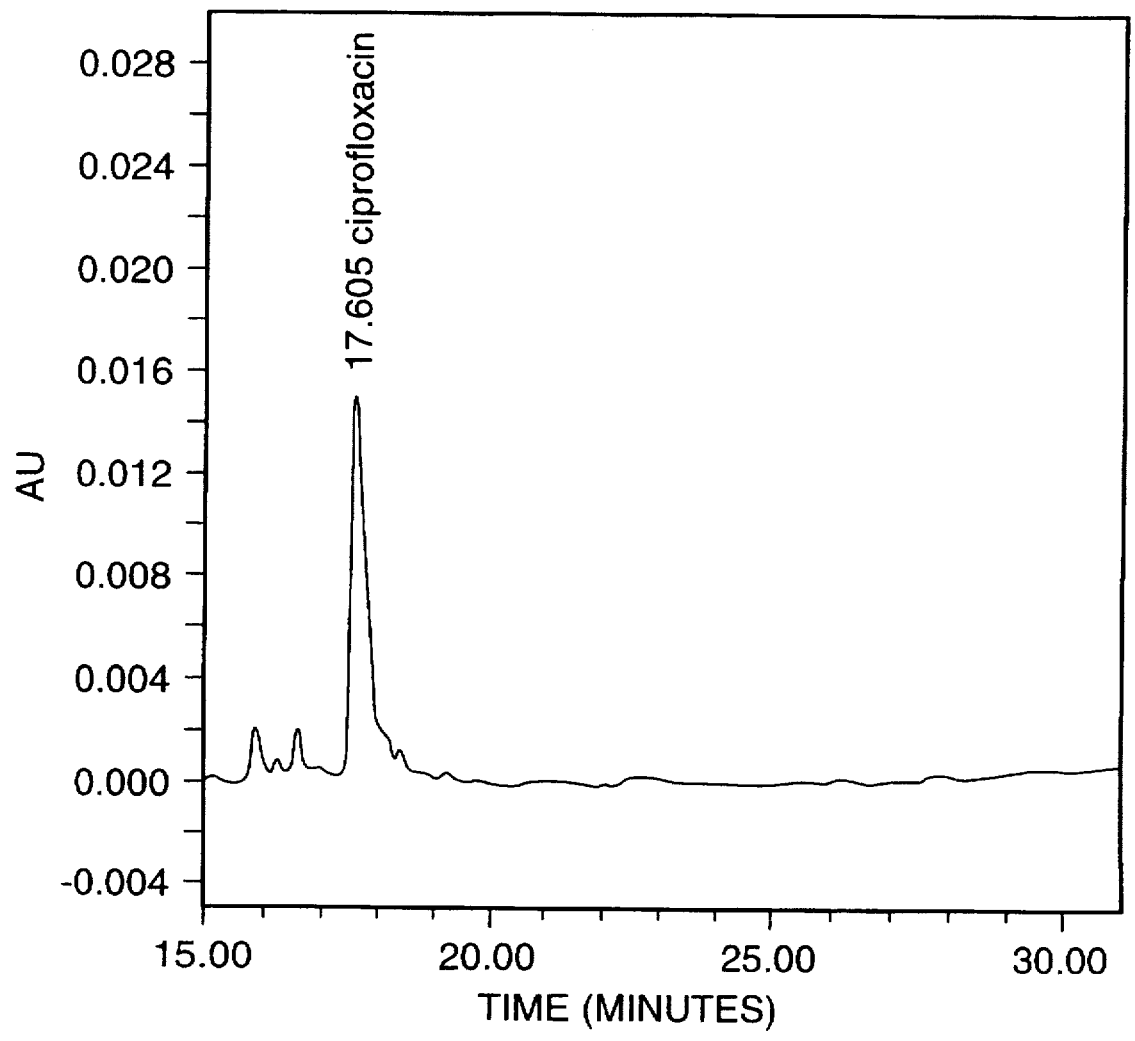

Polymer S12 was then used to evaluate the ability of the an hydrolytic enzyme to degrade the material and preferentially release drug. Polymer S12 was coated onto small glass cylinders, then incubated in the presence and absence of hydrolytic enzyme (i.e. cholesterol esterase for up to 28 days at 37° C. At various time intervals standard aliquots were removed from the polymer S12 incubation solution and assayed via high pressure liquid chromatography (HPLC). Standard aliquots of pure ciprofloxacin HCl were run through an HPLC system and the UV spectrum of each of the compounts were acquired. FIG. 10 shows the HPLC chromatogram for a standard sample of ciprofloxacin HCl drug. The peak of the standard shows up at approximately 17 minutes. FIG. 11 shows the BPLC chromatogram for samples isolated from the buffer control solution. This chromatogram was recorded at 280 nm wavelength from the UV spectrum. FIG. 12 shows the HPLC chromatogram for samples isolated from the enzyme solution. The peak area for the drug peak (at 17 minutes) is approximately 10 times greater for samples incubated with enzyme (FIG. 12) than for buffer controls (FIG. 11). This clearly illustrates the potential for drug delivery under conditions representing the hydrolytic action of the body's host response.

The same S12 polymer incubation solutions assayed via HPLC were also evaluated for antimicrobial activity using a biological assay. A macrodilution minimum inhibitionary concentration (MIC) assay was employed to determine the concentration of antimicrobial (ciprofloxacin) that would inhibit the growth of a pathogen often associated with device-related infections, *Pseudomonas aeruzinosa*. The MIC for this organism and ciprofloxacin was determined to be 0.5 µg/mL. Incubation solutions from both enzyme and buffer control treatment of the polymer S12 were used in a biological assay matrix that was designed to estimate the concentration of ciprofloxacin as a function of incubation time and treatment. The data are presented in Table 1. Antimicrobial activity was not detected in any of the replicate S12 polymers exposed to buffer (control) incubation solutions. However, the enzyme-treated S12 polymers released clinically significant (>MIC levels) of antibiotic over the 28 day incubation period. These biological assay data show a significant correlation with the HPLC data described above. The results of these experiments demonstrate that the antibiotic agent is released from S12 polymer under enzymatic activation, and that the antibiotic has antimicrobial activity against a clinically significant bacterium. Furthermore, clinically significant concentrations ($\geq$MIC levels) of the antibiotic are released over an extended period of time, 28 days.

TABLE 1

Ciprofloxacin antimicrobial levels in S12 polymer incubation solutions. Concentration values (in µg/mL) were determined from MIC assays.

|  | Incubation Time, Days | | | | |
|---|---|---|---|---|---|
| Treatment (Replicate #) | 0 | 7 | 14 | 21 | 28 |
| S12 Control (1) | <0.5 | <0.5 | <0.5 | <0.5 | <0.5 |
| S12 Control (2) | <0.5 | <0.5 | <0.5 | <0.5 | <0.5 |
| S12 Control (3) | <0.5 | <0.5 | <0.5 | <0.5 | <0.5 |
| S12 Enzyme (1) | <0.5 | 0.5 | 0.5 | 0.5 | 0.5 |
| S12 Enzyme (2) | <0.5 | 1 | 1 | 1 | 1 |
| S12 Enzyme (3) | <0.5 | 1 | 1 | 1 | 1 |

Example 7

This example (S7) is similar to the material in Example S5 except that 60 mg of catalyst were used and the reaction was carried out in nitrogen controlled atmosphere. In addition, a temperature controller device was used to maintain more control on the reaction vessel at 60° C. During reaction, polymer began to precipitate out of the reaction solution two hours after the addition of Jeffamine-900 polyether diamine. The final polymer was yellow and elastomeric and was purified by washing/precipitation steps and then tested for its anti-microbial effect on *P. aeruginosa*, a significant clinical pathogen associated with AD.

Biological Method

A series of borosilicate glass cylinders (1 cm length, 2 mm I.D., 3 mm O.D) were coated with antimicrobial co-polymer using a solution of DMAC and polymer for the coating step. Uncoated glass cylinders were employed as substrate controls. The coated and uncoated cylinders were placed in a minimal volume of either physiological saline, pH 7.2 or an enzyme/physiological saline solution. Coated cylinders in the "test solution", were stored at 37° C. for up to 24 days. At various time intervals, an aliquot of the test solution was removed to polystyrene microtitre plates containing Mueller-Hinton broth. The remaining test solution volumes were archived in polypropylene tubes and frozen at –70° C.

until required for liquid chromatography analysis. A similar volume of either physiological saline or enzyme solution was used to replenish the respective coated cylinder solutions.

Figure 13:
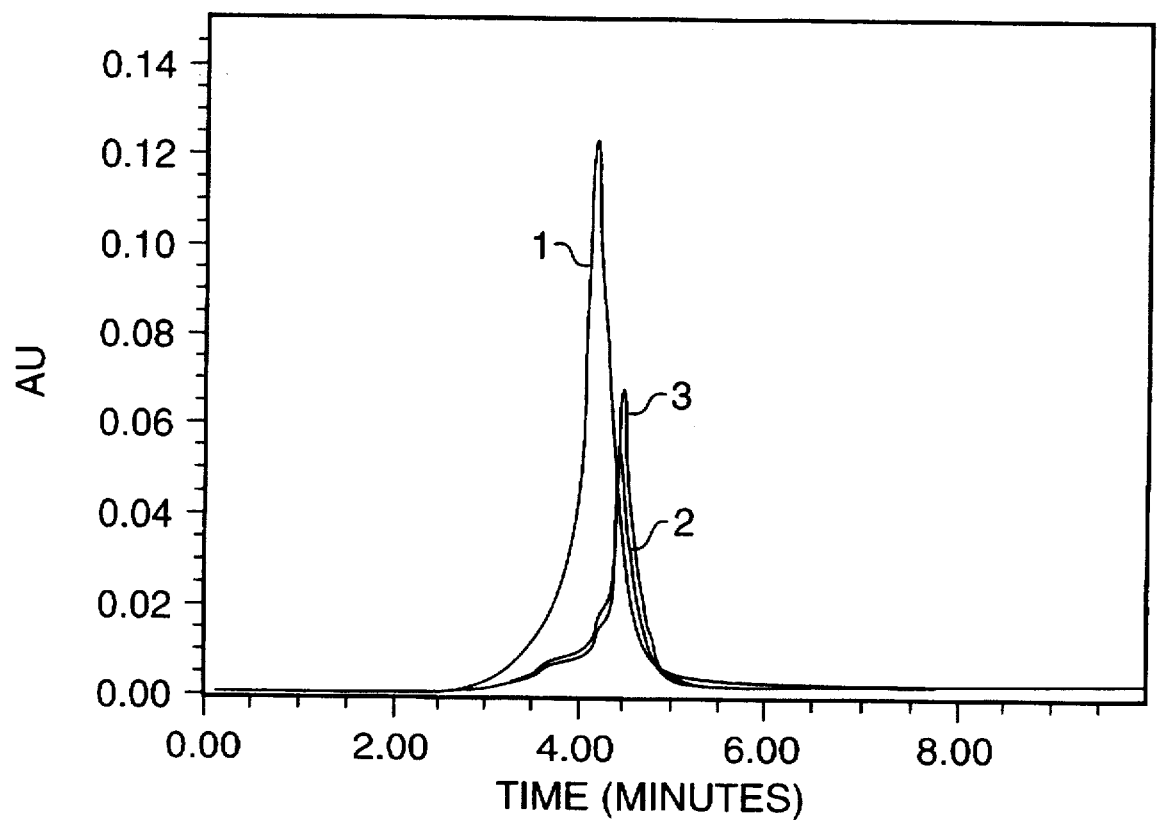
Figure 14:
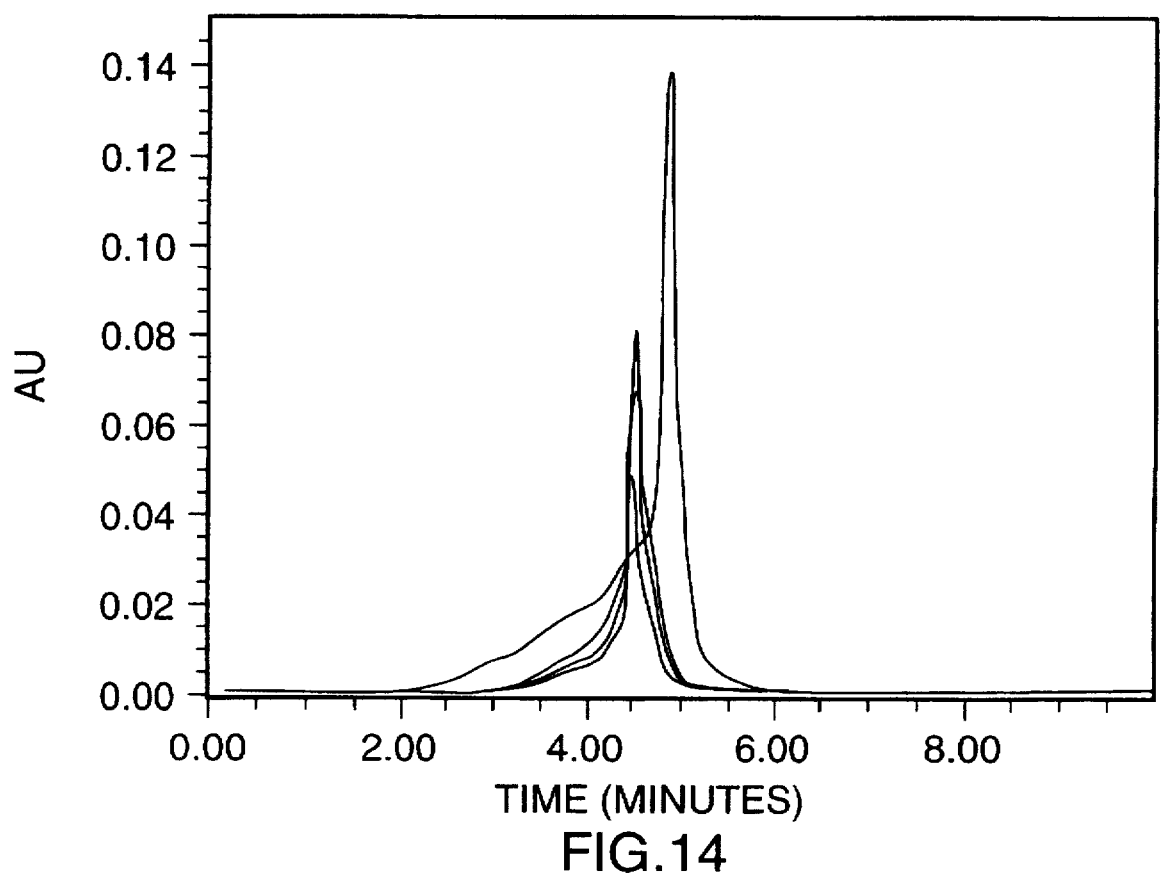

The incubation solutions, with and without enzyme for time zero and a standard aliquot of pure ciprofloxacin HCl were run through a high performance liquid chromatographic system and the UV spectrum of each of the compounds was acquired. FIG. 13 shows a chromatogram for the incubation solutions with (peak 2) and without (peak 3) enzyme at time 0 and 37° C. These are compared to a ciprofloxacin standard (peak 1). There is only one peak present for the pure standard and the incubation samples, at a wavelength of 280 nm. The peak of the standard is slightly shifted relative to that of the incubation samples and this shift is related to slight differences in the chromatograph mobile phases from one day to the next. The results show that at time zero, the amount of ciprofloxacin found in both incubation solutions is similar. Incubation solutions obtained from the buffer incubations (no enzyme) at time 0, 72 hours, 9 days and 18 days were run on the HPLC and the data are shown in FIG. 14. The drug polymer shows its highest release of ciprofloxacin at 72 hours, wherein the equivalent of 40 µg/mL of ciprofloxacin is released. After 72 hours, the amount of ciprofloxacin release is lower, but is still significant.

| Sample Name Cipro | Ret Time (min.) | Area (uV* sec) | Amount |
|---|---|---|---|
| s7con.18d | 4.437 | 1156538 | 11.380 |
| s7con.9d | 4.453 | 1941569 | 18.982 |
| s7con.0 | 4.455 | 1563129 | 15.317 |
| s7con.72 | 4.755 | 4149669 | 40.364 |

Figure 15:
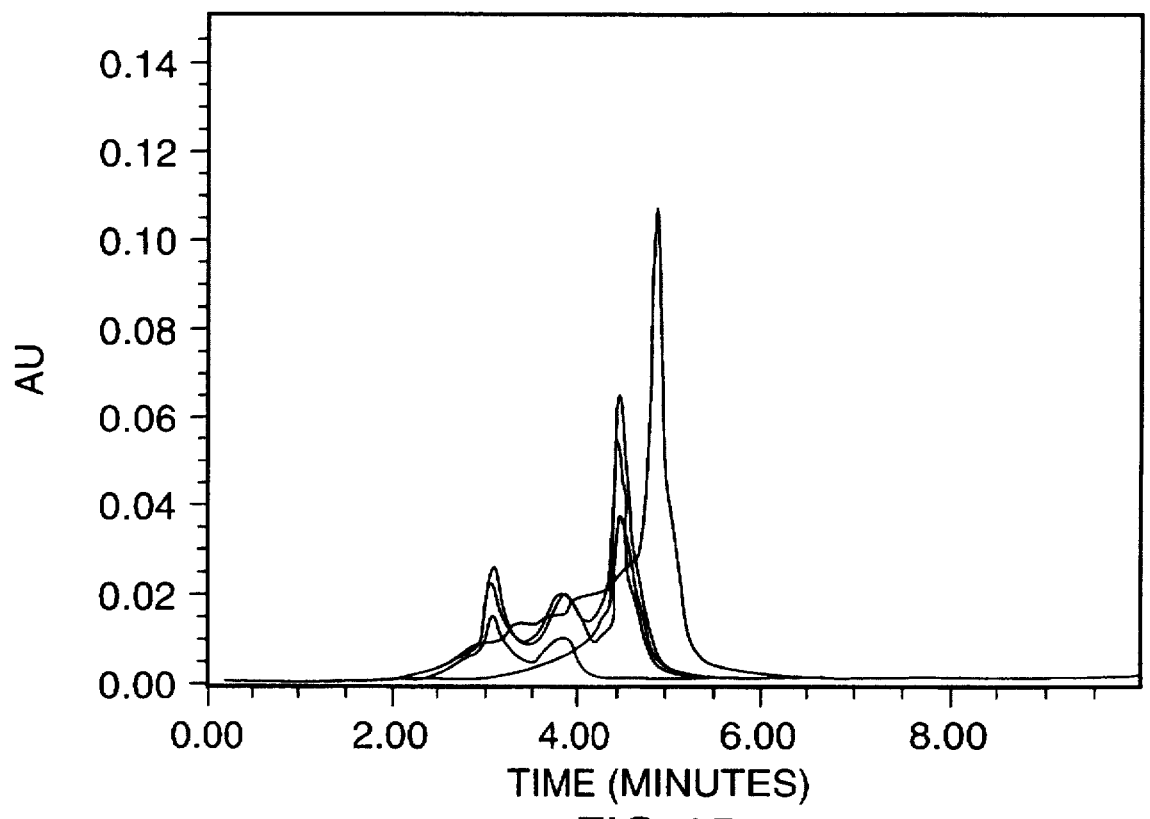

Incubation solutions obtained from enzyme incubations at time 0, 72 hours, 9 days and 18 days were also run on the HPLC and the data are shown in FIG. 15. Also included in FIG. 15 is a glass enzyme control which was incubated for 9 days. This sample contained no drug polymer but was replenished with enzyme at the same time as the enzyme incubated polymer solutions. While the enzyme processing cleaned up the bulk of the enzyme, it is apparent that some residual low molecular weight material remained and accounted for the peaks at 3 and 3.7 minutes. Since this sample had no drug polymer, there is no observable peak at >4 minutes, associated with ciprofloxacin. Again, the polymer incubated for 72 hours shows the highest ciprofloxacin peak at 4.5-5 minutes and the amounts of observed ciprofloxacin were similar in magnitude to those of the buffer incubated solutions, for all time points.

| Ret. Time (min.) | Area (uV* sec) | Amount | Sample Name |
|---|---|---|---|
| 4.220 | no peak | no peak | enzyme control |
| 4.438 | 1257141 | 12.354 | polymer/CE 0 days |
| 4.455 | 1254240 | 12.326 | polymer/CE 9 days |
| 4.470 | 698737 | 6.947 | polymer/CE 18 hours |
| 4.471 | 3522680 | 34.292 | polymer/CE 72 hours |

These data indicate that this particular formulation of the drug polymer is hydrolytically degraded by the buffer solution at 37° C., and that the enzyme was not preferentially degrading the polymer.

Example 8

Figure 16:
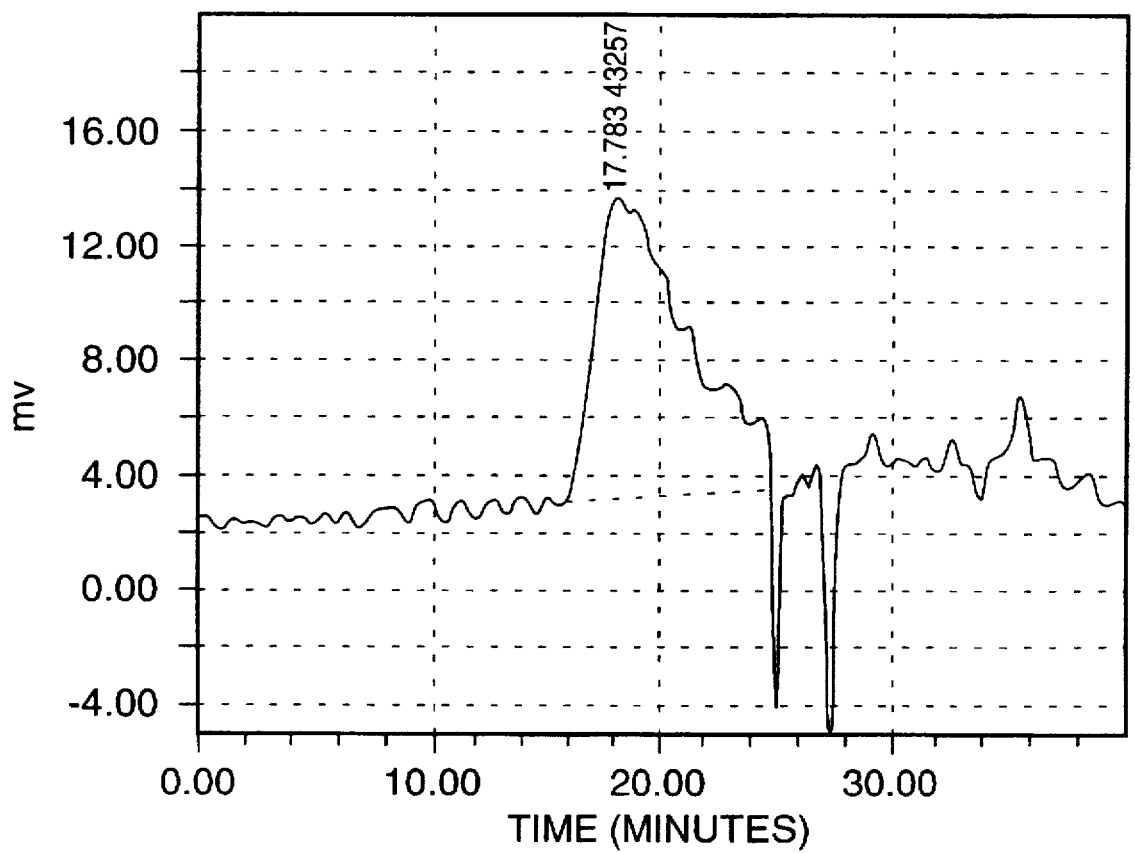

This example (S8) is similar to the material in Example S7 except that the reaction was carried out in the presence of an acid scavenger, namely, triethylamine (TEA). TEA takes-up the HCl from the ciprofloxacin as the polymerization proceeds. This increases the molecular weight of the polymer, eliminates the bimodal peaks observed in example S5 and increases the amount of ciprofloxacin incorporated into the polymer. The polymer was precipitated in water and washed three time with distilled water with overnight stirring. The final polymer was a yellow elastomeric type material. Its gel permeation chromatogram is shown in FIG. 16. The weight average molecular weight is approximately $3.0 \times 10^4$ and the polymer no longer has a bimodal peak. Following the various washing steps, the wash solutions were analysed by HPLC for the presence of ciprofloxacin (FIG. 17).

| Ret. Time (min.) | Area (UV*sec) | Amount | Sample Description |
|---|---|---|---|
| 4.287 | 38554 | 0.554 | After 3rd wash |
| 4.288 | 54868 | 0.712 | After 2nd wash |
| 4.335 | 191775 | 2.038 | After 3rd wash |

Figure 17:
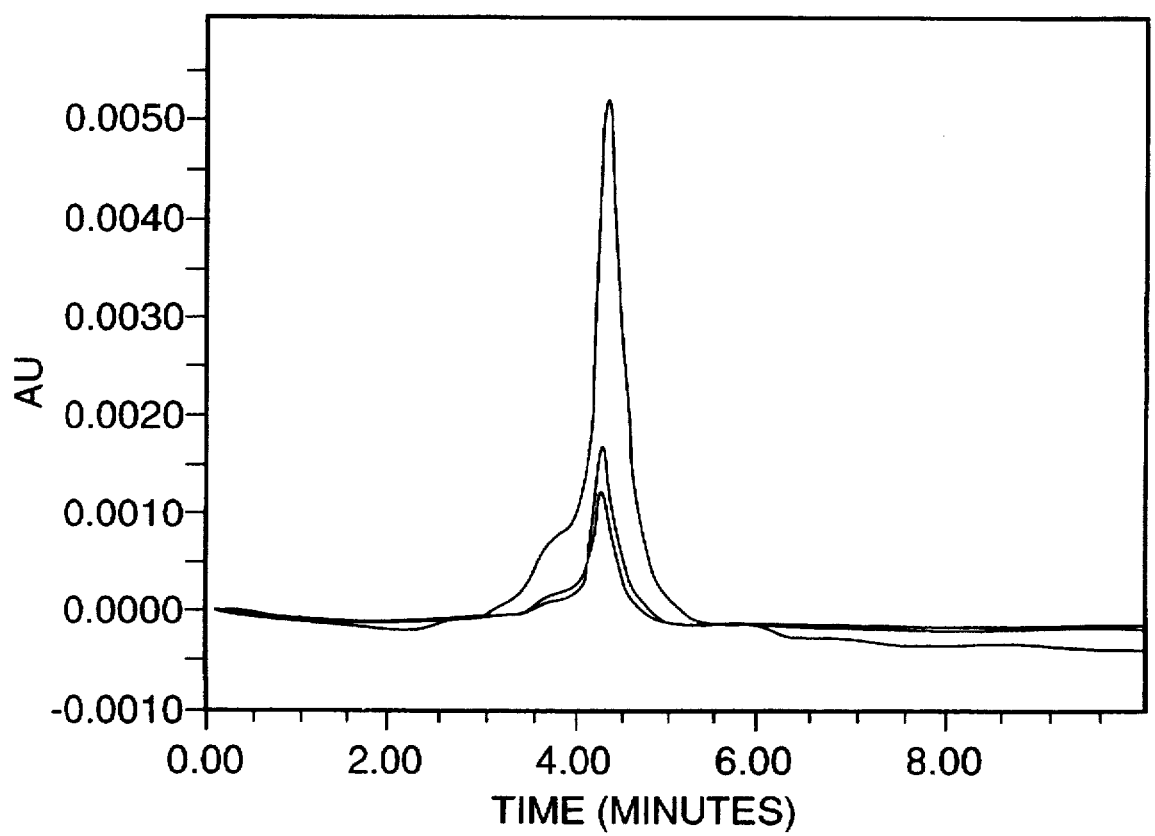
Figure 18:
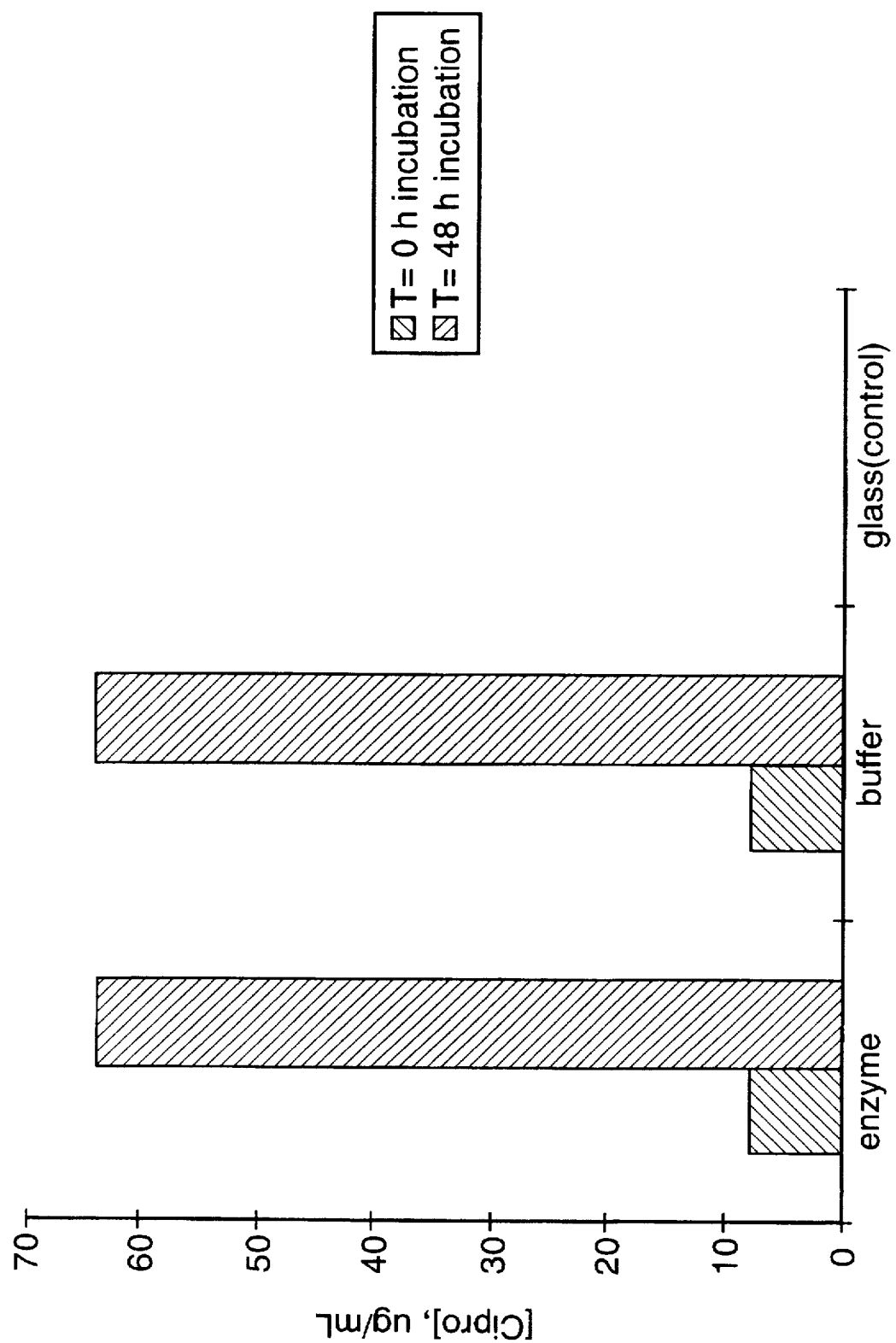
FIG. 18 is a chart showing ciprofloxacin release before and after an incubation period for various systems.

As is shown in FIG. 17 the amount of unreacted ciprofloxacin is dramatically reduced after the first wash. These levels suggest that following washing there are approximately 10 µg of residual ciprofloxacin per gram of drug polymer. Incubation experiments and assessment of antimicrobial action, similar to those carried out in Example 7, generated in excess of 64 µg/mL of ciprofloxacin after 48 hours of incubation time (FIG. 18) for 0.35 grams of drug polymer. Based on FIG. 17, the maximum amount of residual free drug that could be leached from all of the drug polymer for 0.35 grams of drug polymer in 3 mLs of incubation solution (amount contained in the vacutainers) is approximately 1 µg/mL. This value is significantly less than the detected amount of >64 µg/mL and clearly suggests that hydrolysis of the polymer and subsequent release of covalently bound drug is occurring. The effect of the released antimicrobial agent on the P. aeruginosa bacteria (FIG. 18) is similar to that observed in Example 7 and provides furter evidence of the ability of the released drug to kill the bacteria.

A MIC assay was performed on the test solutions using previously published method (16). Two-fold dilutions of the test solution were made in Mueller-Hinton broth. An inoculum consisting of a 24 h broth culture of a clinical isolate of P. aeruginosa was added to each of the test solution dilutions. The inoculated test solutions were incubated 24 h at 37° C. Following the incubation period, the broth solutions were observed for growth as shown by the development of a visible turbidity. The highest dilution of test solution showing no growth was defined as the minimum inhibitory concentration (MIC). Control experiments with this test organism and ciprofloxacin established a minimum inhibitory concentration of 0.5 µg/mL.

Results

The results of the antimicrobial efficacy analyses are shown in Table 2 and give a concentration range related to equivalents of ciprofloxacin HCl present, based on the serial dilution of incubation media required to correspond to the MIC for ciprofloxacin HCl. The data indicate that the BR-PAC exhibited efficacy against P. aeruginosa for a minimum of 24 days. The presence of hydrolytic enzyme activity did not significantly influence the anti-microbial efficacy.

TABLE 2

Concentration of antibiotic present in test solutions as a function of exposure time.

| Exposure Time, days at 37° C. | Uncoated Glass + Enzyme solution, µg/mL antibiotic | Coated Glass + Saline, mg/ml antibiotic | Coated Glass + Enzyme Solution, µg/mL antibiotic |
|---|---|---|---|
| 0 | <2 | 32–128 | 32–128 |
| 3 | <2 | 32–128 | 32–128 |
| 10 | <2 | 32–128 | 32–128 |
| 17 | <2 | 16–32 | 4–8 |
| 24 | <2 | 8–16 | 8–16 |

Example 9

This example (S14) is similar to polymer S12 except that the diisocyanate was substituted for HDI. hexamethylene-diisocyanate (HDI) was used (0.35 g) to react with ciprofloxacin HCl (0.4 grams) and polycaprolactone-diol (PCL) of molecular weight 2000 (2.08 grams). The BR-PAC was made using a 2:1:1 stoichiometric combination of the above respective compounds, combined with 6 mg of the catalyst (dibutyltin dilaurate). The material synthesis was carried out by first forming a prepolymer by reaction of PCL with DDI and tin catalyst, at 65° C. for 3 hours in DMSO. Subsequently the ciprofloxacin HCl was dissolved in dimethylsulfoxide solvent, heating to 70° C. and then adding triethylamine. The ciprofloxacin solution was reacted with the prepolymer for 40 hours at 65° C. The complete reaction was carried out in a tin foiled covered reactor in order to reduce the degradation of the drug in the presence of light. This polymer remained in solution until the reaction vessel was cooled to room temperature. The synthesized materials were then washed with distilled water and dried at 50° C. in a vacuum oven. The final polymer was yellow and elastomeric in nature. The polymer was easily precipitated in water, and yields greater than 70% were obtained. The weight average polystyrene equivalent molecular weight was $2.4 \times 10^4$.

Figure 19:
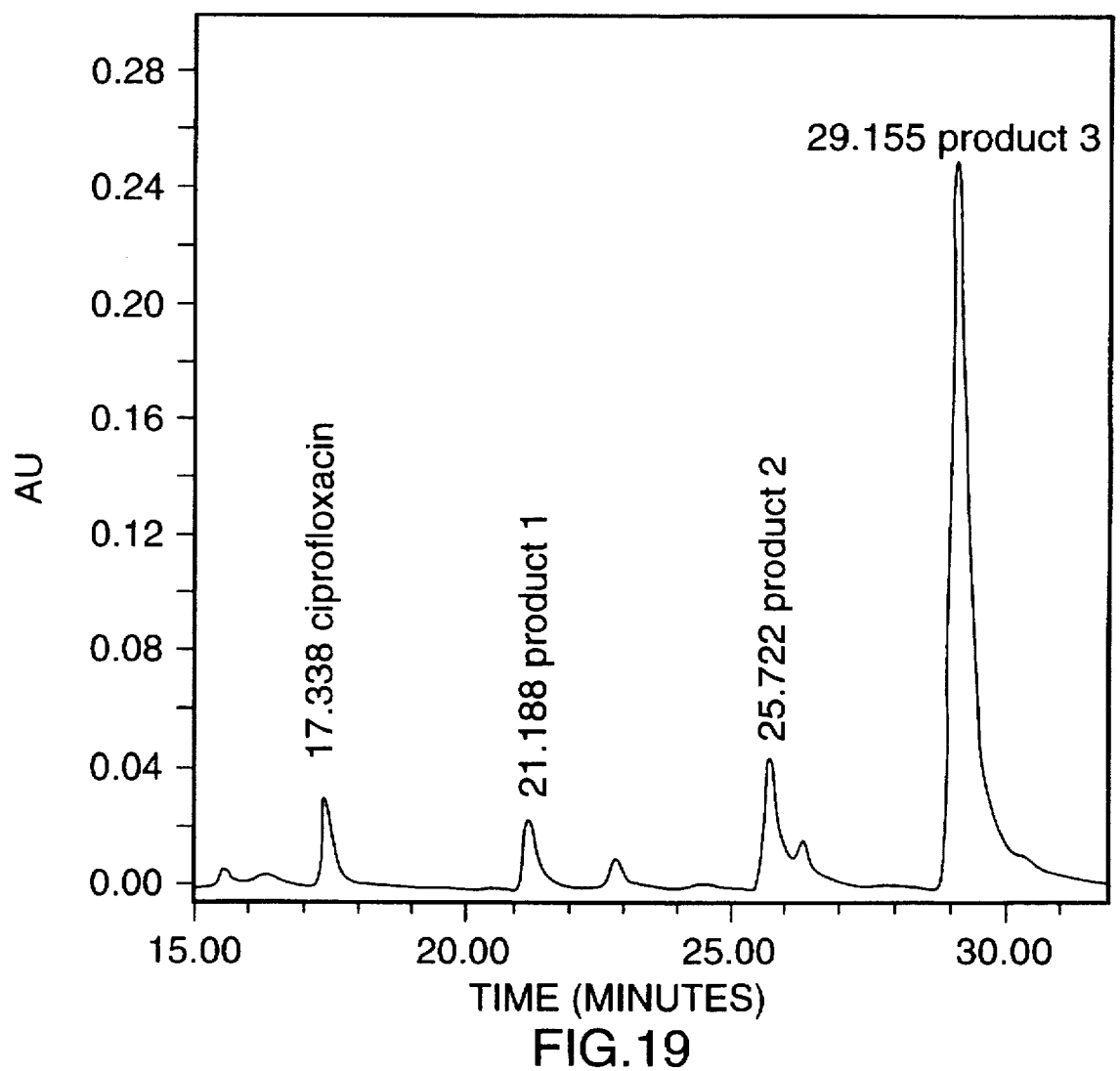
Figure 20:
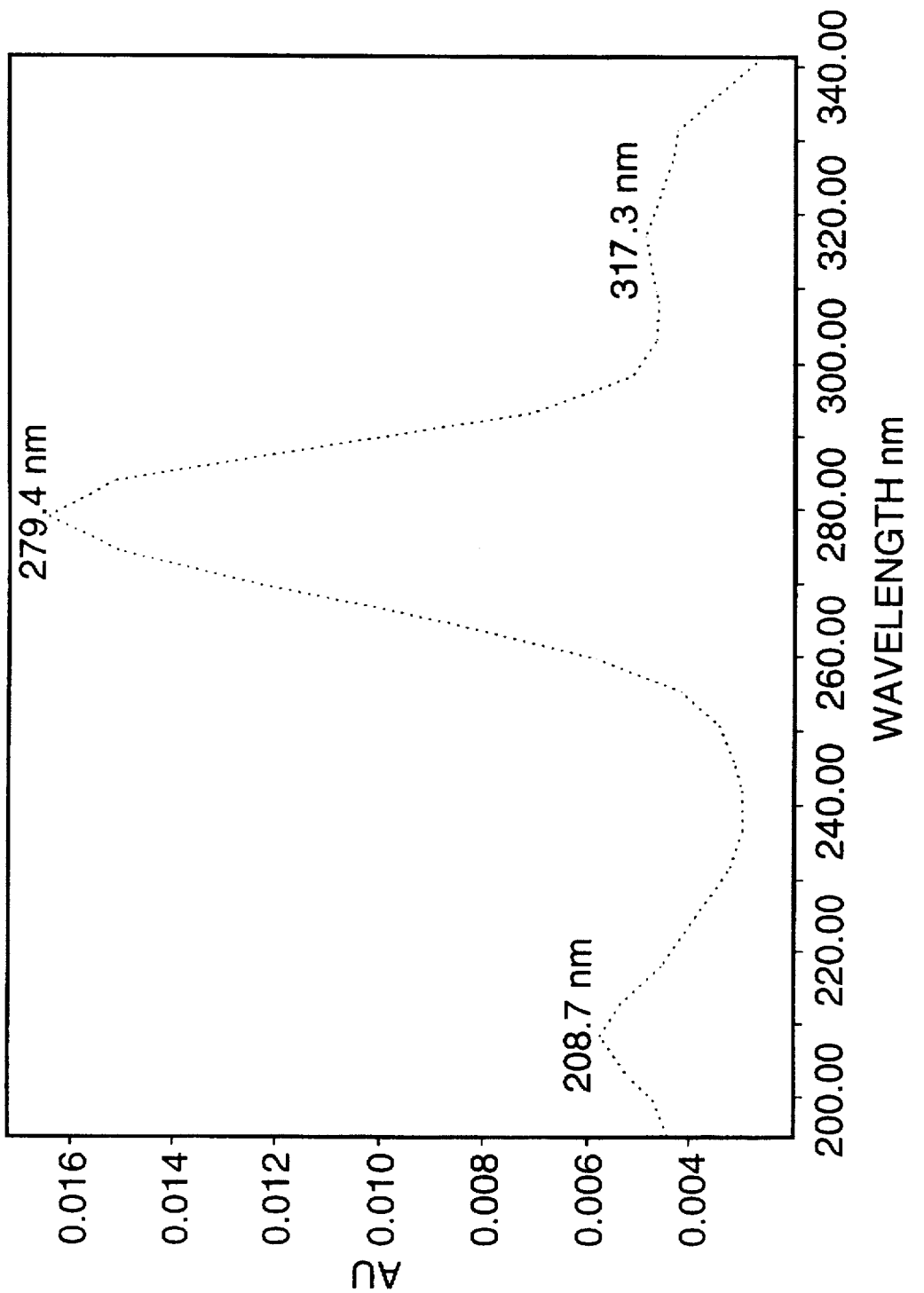
Figure 21:
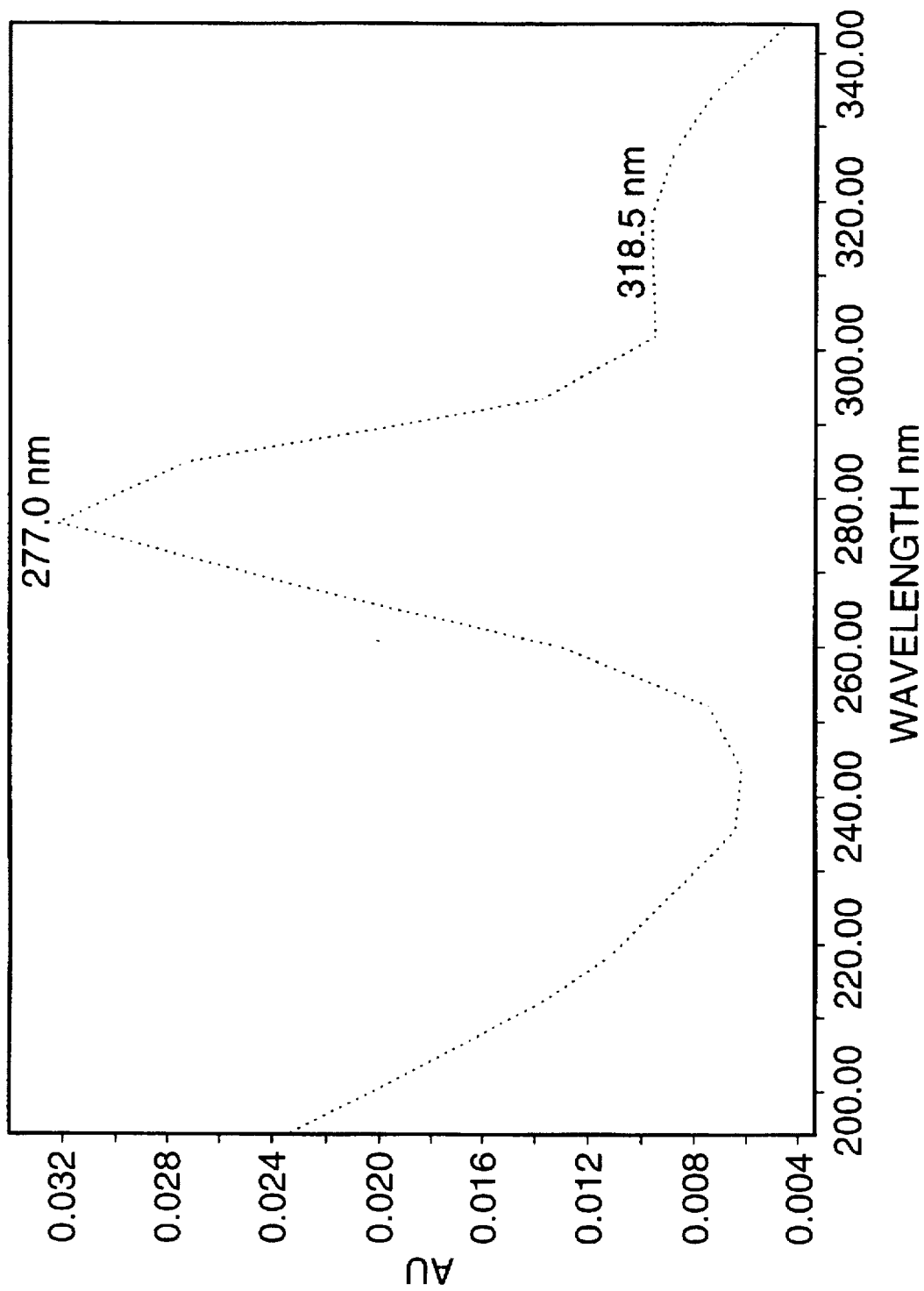
Figure 22:
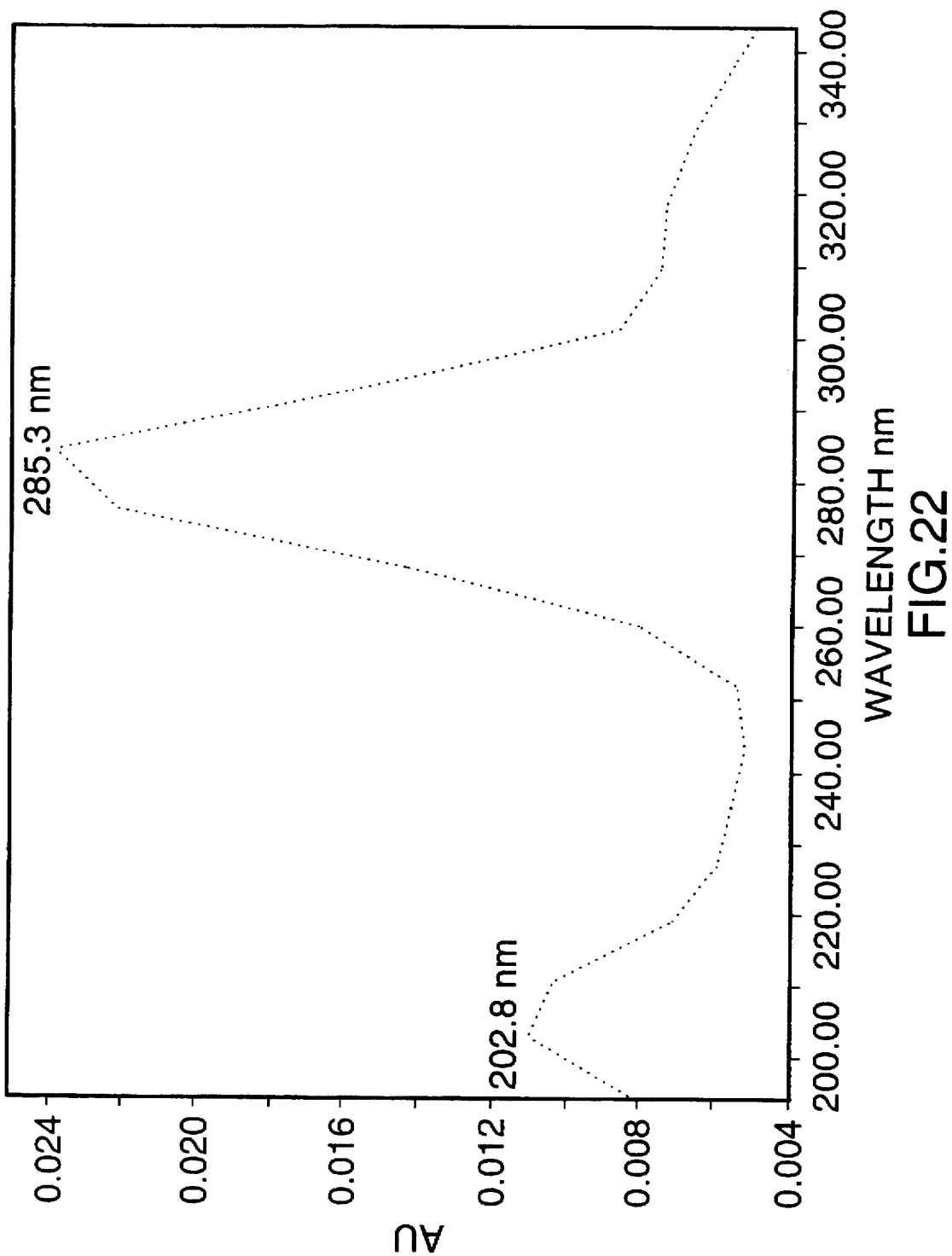
Figure 23:
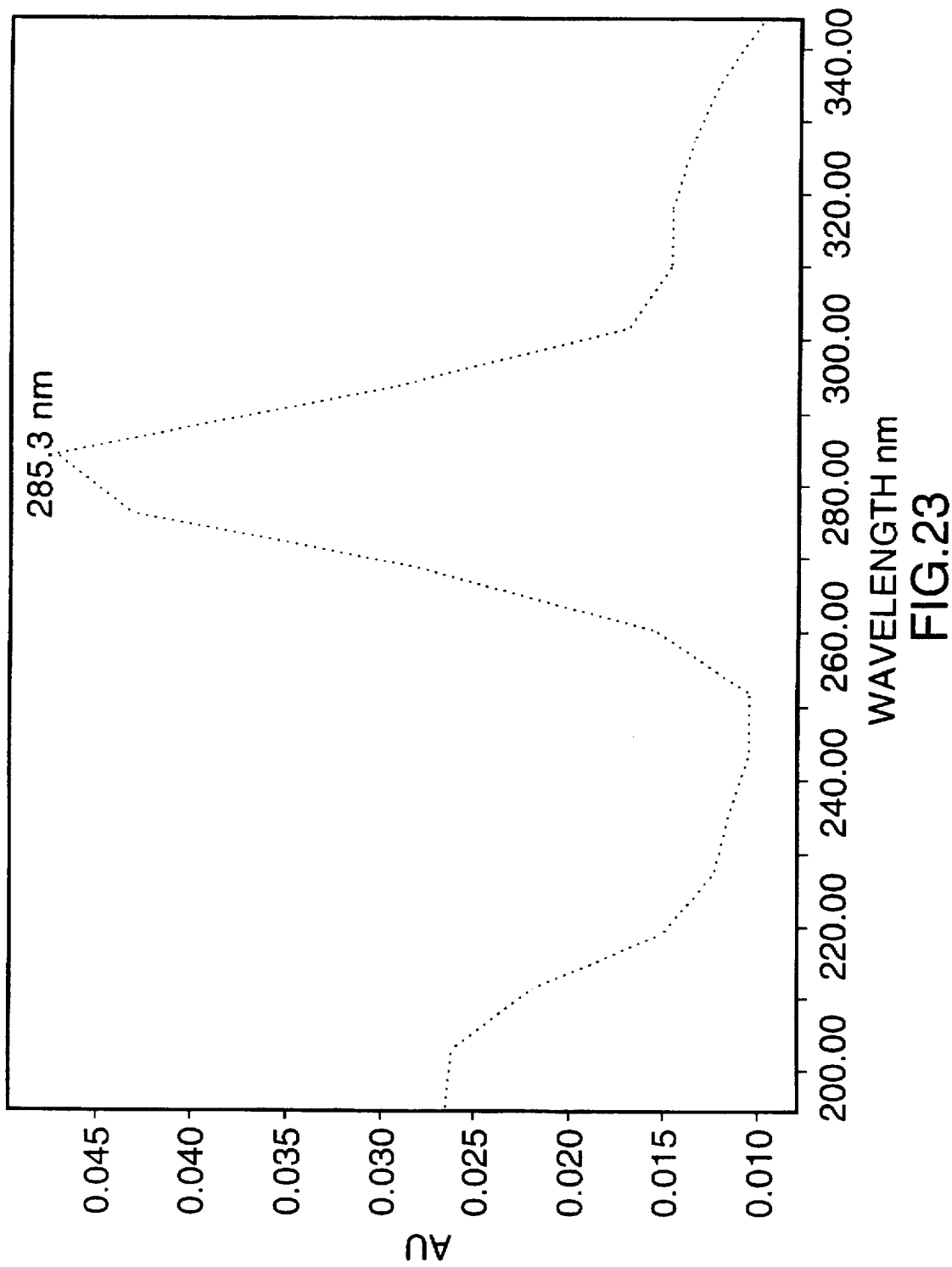
Figure 24:
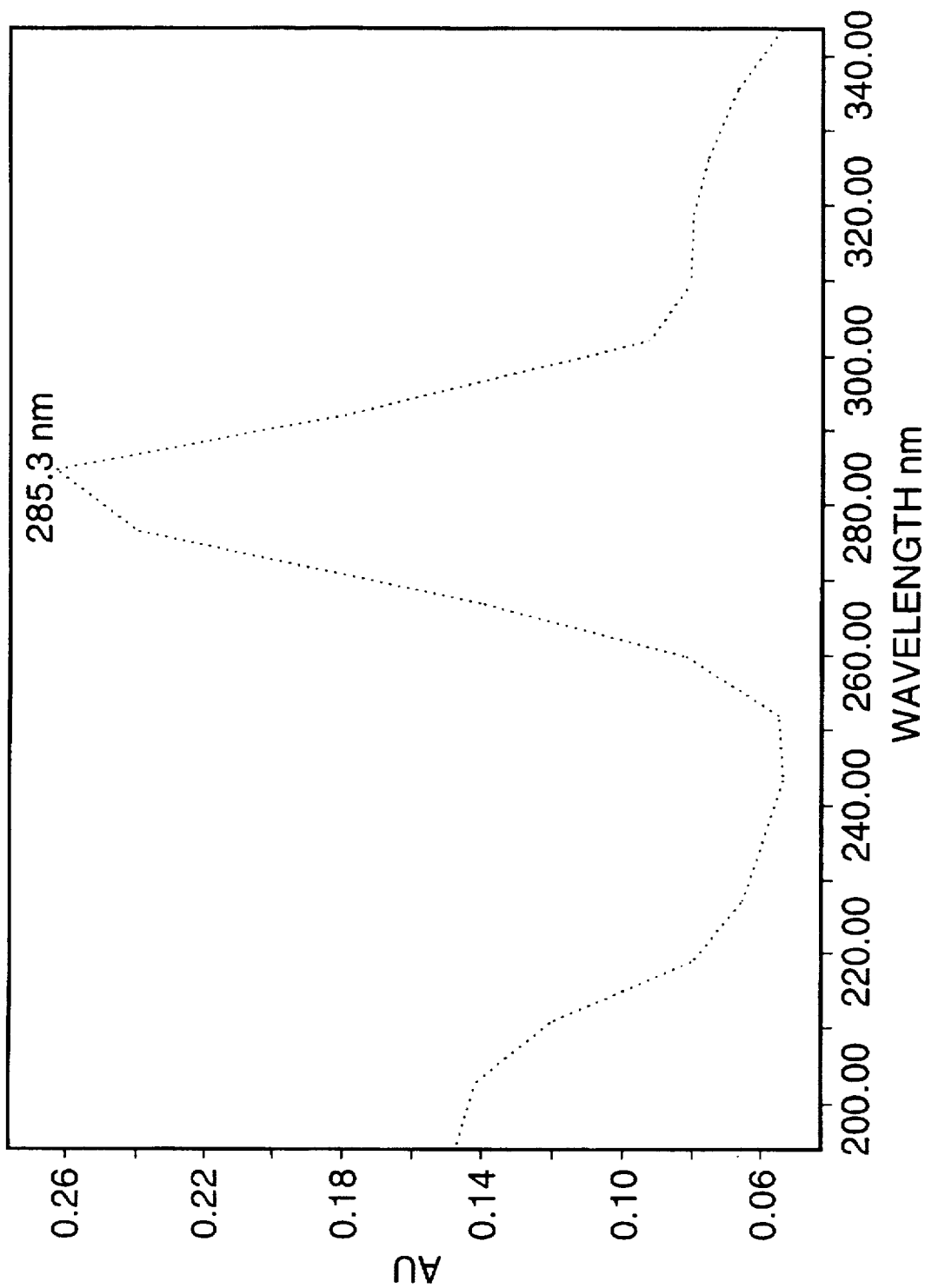

Polymer S14 was then used to evaluate the ability of a hydrolytic enzyme to degrade the material and preferentially release drug. The incubation solutions (with and without enzyme (CE)) after 7 days incubation and a standard aliquot of pure ciprofloxacin HCl were run through a HPLC system and the UV spectrum of each of the compounds were acquired. FIG. 19 shows the HPLC chromatogram for the enzyme treated sample. This chromatogram was recorded at 280 nm wavelength from the UV spectrum. In this Figure it is clearly demonstrated that the polymer is breaking down into several products and must contain the drug component since it is the only monomer component of the polymer that absorbs UV at 280 nm. FIG. 20 shows the UV spectrum of a ciprofloxacin HCl standard and FIGS. 21–24 show the UV spectrum of four dominant peaks from FIG. 19. FIGS. 21, 22, 23 and 24, show the peaks of 17.34 min., 21.19 min., 25.72 min. and 29.15 min., respectively, from FIG. 13. These latter UV peaks are all similar to the standard (FIG. 20) and support the claim that the polymer is being degraded by the enzyme which is ultimately resulting in the formation of several products that contain the drug. The presence of pure drug at the retention time of the standard (i.e. 17 minutes in FIG. 19) is indicative that the degradation products ultimately degrade to release the pure drug.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

We claim:

1. A bioresponsive, pharmacologically-active, polymeric material having a polystyrene equivalent molecular weight selected from 2,000–200,000 and a backbone comprising a pharmacologically-active fragment formed from a fluoroquinolone covalently linked through two functional groups selected from a polyamide, polyurea, polyurethane and polysulfonamide formed from two or isocyanate functional groups within said backbone.

2. A polymeric material as defined in claim 1 further comprising one or more polyester, and polyether linkages.

3. A polymeric material as defined in claim 2 wherein said polyester linkage is made from polycaprolactone-diol.

4. A polymeric material as defined in claim 2 wherein said polyether linkage is made from polyether-diamine.

5. A polymeric material as defined in any one of the preceding claims wherein said backbone comprises 1,6-diamidohexane—or 1,12-diamidododecane-polyurethane, -polyurea, polyamide or polysulphonamide linkages.

6. A polymeric material as defined in claim 1 wherein said phannacologically-active fragment provides biological activity selected from the group consisting of anti-inflammatory, anti-bacterial, anti-microbial and anti-fingal activity under in vivo biochemical action.

7. A polymeric material as defined in claim 1 wherein said fluoroquinolin is ciprofloxacin (1-cyclopropyl-6-fluoro-1,4-dihydro-4-oxo-7-piperazine-quinolone-3-carboxylic acid).

8. A polymeric material as defined in claim 1 made by the reaction of a polyisocyanate, an oligomeric α-ω diol, diamine or amino-alcohol, and a covalently linkable pharmacologically-active compound.

9. A polymeric material as defined in claim 1 wherein said polyisocyanate is selected from hexamethylene diisocyanate and dodecyl-diisocyanate; said oligomeric diol is polycaprolactone-diol; and said pharmacologically-active compound is an antibacterial fluoroquinolone.

10. A polymeric material as defined in claim 9 made by (a) reacting said hexamethylene diisocyanate or dodecyl-diisocyanate with polycaprolactone-diol to form a prepolymer; and (b) reacting said prepolymer with ciprofloxacin.

11. A solid substrate comprising in whole or in part a bioresponsive pharmacologically-active polymeric material as defined in claim 1.

12. A solid substrate wholly or partially coated with a bioresponsive pharmacologically-active polymeric material as defined in claim 1.

13. A substrate as defined in claim 11 from the group consisting of an access device, suture, film, patch and dental fibre.

14. A method of delivering a bioresponsive pharmacologically-active compound to a selected site in a mammal, said method comprising, locating or disposing a polymeric material as defined in claim 1, at or adjacent the locus of said site.

15. A method of delivering a bioresponsive pharmacologically-active compound to a selected site in a mammal, said method comprising, locating or disposing a substrate as defined in claim 11 at or adjacent the locus of said site.

* * * * *